(12) United States Patent
Petrenko et al.

(10) Patent No.: US 9,226,972 B2
(45) Date of Patent: Jan. 5, 2016

(54) TARGETED PARTICLES COMPRISING LANDSCAPE PHAGE FUSION PROTEINS AND HETEROLOGOUS NUCLEIC ACID

(75) Inventors: Valery A. Petrenko, Auburn, AL (US); Deepa Bedi, Auburn, AL (US); Olusegun A. Fagbohun, Auburn, AL (US); James W. Gillespie, Simpsonville, SC (US)

(73) Assignee: Auburn University, Auburn, AL (US)

( * ) Notice: Subject to any disclaimer, the term of this patent is extended or adjusted under 35 U.S.C. 154(b) by 148 days.

(21) Appl. No.: 13/695,570

(22) PCT Filed: May 5, 2011

(86) PCT No.: PCT/US2011/035390
§ 371 (c)(1),
(2), (4) Date: Mar. 13, 2013

(87) PCT Pub. No.: WO2011/140365
PCT Pub. Date: Nov. 10, 2011

(65) Prior Publication Data
US 2013/0202679 A1    Aug. 8, 2013

Related U.S. Application Data

(60) Provisional application No. 61/331,583, filed on May 5, 2010.

(51) Int. Cl.
| | | |
|---|---|---|
| *A61K 9/127* | (2006.01) | |
| *C07K 4/00* | (2006.01) | |
| *C07K 14/01* | (2006.01) | |
| *C07H 21/02* | (2006.01) | |
| *C07H 21/04* | (2006.01) | |
| *A61K 48/00* | (2006.01) | |
| *A61K 47/48* | (2006.01) | |
| *C12N 15/113* | (2010.01) | |
| *A61K 31/704* | (2006.01) | |
| *A61K 31/713* | (2006.01) | |

(52) U.S. Cl.
CPC ......... *A61K 47/48246* (2013.01); *A61K 31/704* (2013.01); *A61K 31/713* (2013.01); *A61K 47/48776* (2013.01); *C12N 15/113* (2013.01); *C12N 15/1137* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 7,670,765 B2 | 3/2010 | Petrenko et al. | |
| 8,137,693 B2 | 3/2012 | Petrenko | |
| 8,252,324 B2 | 8/2012 | Petrenko | |
| 2003/0113320 A1* | 6/2003 | Ruoslahti et al. | 424/143.1 |
| 2005/0246794 A1* | 11/2005 | Khvorova et al. | 800/286 |
| 2007/0077291 A1* | 4/2007 | Petrenko | 424/450 |

FOREIGN PATENT DOCUMENTS

| | | |
|---|---|---|
| WO | 2007118245 | 10/2007 |
| WO | 2011050178 | 4/2011 |

OTHER PUBLICATIONS

Mount et al (Gene 341 (2004) 59-65).*
Li et al (Biochemistry 2007, 46, 8579-8591).*
International Preliminary Report on Patentability for PCT/US2011/035390 dated Nov. 15, 2012.
Bedi et al., "Delivery of siRNA into breast cancer cells via phage fusion protein-targeted liposomes", Nanomedicine: Nanotechnology, Biology and Medicine, Jun. 1, 2011, 7(3):315-323.
Jayanna et al., "Liposomes targeted by fusion phage proteins", Nanomedicine: Nanotechnology, Biology and Medicine, Mar. 1, 2009, 5(1):83-89.
Jayanna et al., "Landscape phage fusion protein-mediated targeting of nanomedicines enhances their prostate tumor cell association and cytotoxic efficiency", Nanomedicine: Nanotechnology, Biology and Medicine, Aug. 1, 2010, 6 (4):538-546.
Sioud, "Targeted delivery of antisense oligonucleotides and siRNAs into mammalian cells", Methods in Molecular Biology, Oct. 10, 2008, 487:61-82.
International Search Report for PCT/US2011/035390 dated Aug. 11, 2011.
Written Opinion for PCT/US2011/035390 dated Aug. 11, 2011.

* cited by examiner

*Primary Examiner* — Richard Schnizer
(74) *Attorney, Agent, or Firm* — Andrus Intellectual Property Law, LLP

(57) ABSTRACT

Disclosed are targeted particles comprising or consisting of a plurality of landscape phage fusion proteins complexed with heterologous nucleic acid, the landscape phage fusion proteins displaying a heterologous peptide and the targeted particle binding specifically to a target site. The particles may be utilized in methods for modulating expression of genes in target cells.

15 Claims, 11 Drawing Sheets

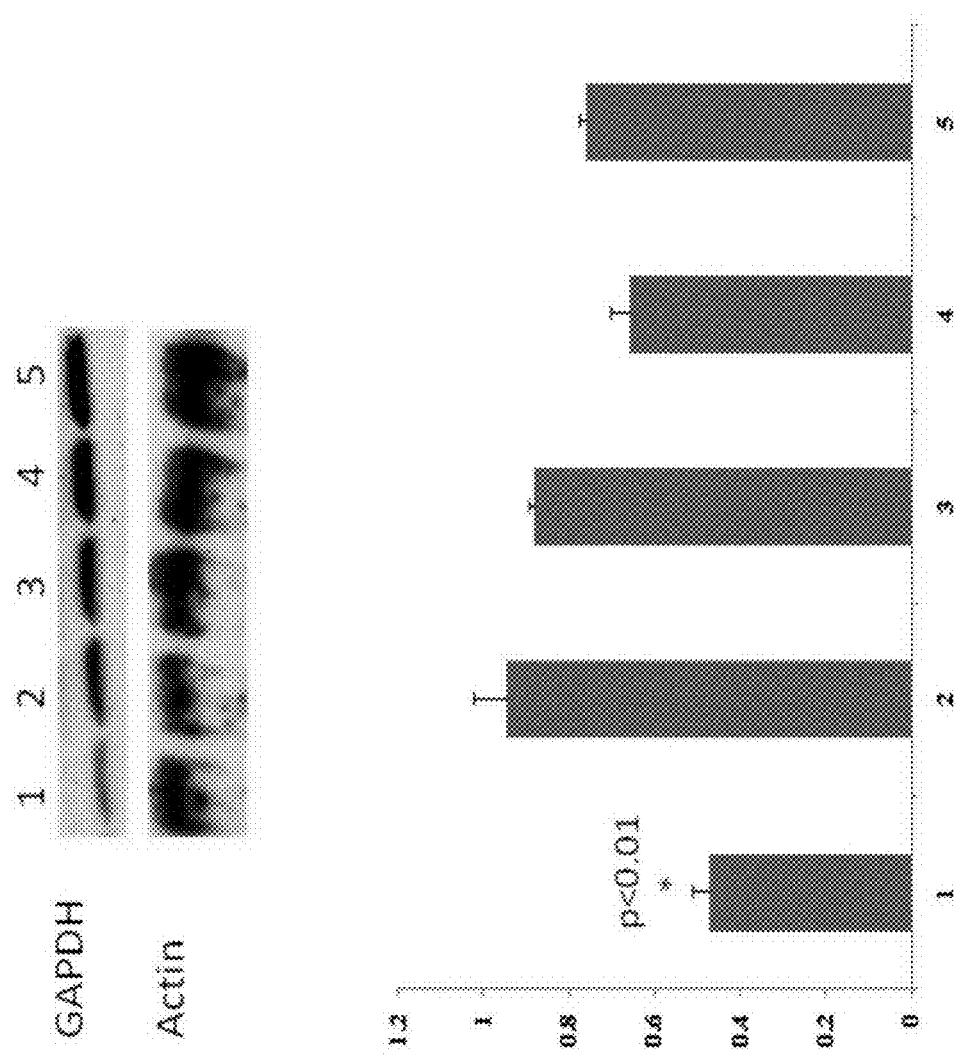

TARGETED PARTICLES COMPRISING LANDSCAPE PHAGE FUSION PROTEINS AND HETEROLOGOUS NUCLEIC ACID

CROSS REFERENCE TO RELATED APPLICATION

The present application is the U.S. national stage application of International Application PCT/US2011/035390, filed May 5, 2011, which international application was published on Nov. 10, 2011, as International Publication WO2011/140365, in the English Language. The International Application claims priority of U.S. Provisional Application No. 61/331,583, filed May 5, 2010, the contents of which are incorporated herein by reference in their entireties.

STATEMENT REGARDING FEDERALLY SPONSORED RESEARCH OR DEVELOPMENT

This invention was made with government support under grant number 5R01 CA125063 awarded by the National Institutes of Health. The government has certain rights in the invention.

BACKGROUND

The field of the invention relates to targeted delivery of nucleic acid. In particular, the field of the invention relates to targeted delivery of nucleic acid such as small inhibitory ribonucleic acid (siRNA) via landscape phage fusion proteins.

The Ff class of filamentous phage includes three strains referred to as f1, fd, and M13. These phages are thread-like particles approximately 1000 nm long and 7 nm in diameter. The majority of the tubular capsid consists of 2700 identical, largely alpha-helical subunits of the ~50-residue pVIII major coat protein. Viral DNA of varying sizes, including recombinant genomes with foreign DNA inserts, can be accommodated in the filamentous capsid whose length is altered to match the size of the enclosed DNA by adding proportionally fewer or more pVIII subunits during phage assembly. Additional phage coat proteins include pIII, pVI, pVII, and pIX. One tip of the phage outer tube is capped with five copies each of the minor coat proteins pVII and pIX and another tip with the minor coat proteins pIII and pVI.

In phage display constructs and libraries formed therefrom, heterologous or foreign coding sequences are spliced in-frame into one of the five phage coat protein genes, so that the 'guest' peptide, encoded by that sequence, is fused to the coat protein to form a fusion protein which displays the guest peptide on the surface of the virion. A phage display library is a collection of such fusion phage clones, each harboring a different foreign coding sequence, and therefore displaying a different guest peptide on their surface. When a foreign coding sequence is spliced into the major coat protein's gene (pVIII), the guest peptide is displayed on every pVIII subunit increasing the virion's total mass by up to 20%. Such particles are generally referred to as "landscape phage" to emphasize the dramatic change in surface architecture caused by arraying thousands of copies of the foreign peptide in a dense, repeating pattern around the viral capsid. A landscape library refers to a large population of such phages, encompassing billions of clones with different surface structures and biophysical properties. Landscape libraries may be screened to identify phage that bind specifically to selected targets such as cancer cells. The fusion proteins isolated from the selected phage can be utilized to target liposomes specifically to these targets. (See U.S. Patent Publication No. U.S. 2007-0077291; and Bedi et al., Nanomedicine 2010 Nov. 2 [Epub ahead of print], PMID:21050894; the contents of which are incorporated herein by reference in their entireties).

Delivery of nucleic acid to target cells holds considerable promise as a therapeutic approach to treating various diseases, for example, via gene therapy or via regulating gene expression. In particular, RNA interference (RNAi) holds considerable promise as a therapeutic approach to silence disease-causing genes. Here, a nanotechnological platform for delivering nucleic acid to target cells is proposed. This platform utilizes the unique propensity of phage proteins to self-assemble in the presence of nucleic acids and to form particles mimicking the structure of the phage capsid.

SUMMARY

Disclosed are targeted particles comprising or consisting of a plurality of landscape phage fusion proteins complexed with heterologous nucleic acid, the landscape phage fusion proteins displaying a heterologous peptide and the targeted particle binding specifically to a target site. The targeted particles may comprise a filamentous phage protein, such as a pVIII major coat protein displaying the heterologous peptide, for example, where the filamentous phage protein and heterologous peptide form a fusion protein. The heterologous peptide is relatively small, for example no more than about 12, 11, 10, 9, or 8 amino acids in length. The disclosed targeted particles may be nanoparticulate with respect to size and having one or more dimensions such as effective diameter or length between about 1 nm and 1000 nm. The complexed nucleic acid may be relatively short in length, for example 10-50 nucleotides in length, and may include siRNA.

The disclosed particles are targeted to specific cellular targets. For example, the disclosed particles may be targeted to one or more cell surface molecules. In some embodiments, the disclosed particles bind specifically to cancer cells or a specific tissue type (e.g., breast cancer cells) but do not bind to non-cancerous cells of the same specific tissue type (e.g., non-cancerous breast cancer cells).

The disclosed particles comprise heterologous nucleic acid such as siRNA for modulating expression of one or more genes in a cell to which the particles are specifically targeted. In some embodiments, the siRNA inhibits expression of one or more genes that are associated with cancer or the risk of developing cancer, or one or more genes that are associated with a cancer cell's resistance to treatment with one or more chemotherapeutic agents. In some embodiments, the targeted particle comprises siRNA that inhibits gene expression of a gene selected from PARP1, MDR1/Pgp, MRP1, and BCRP.

The disclosed particles may be formulated as part of a pharmaceutical composition comprising the targeted particles and a pharmaceutical carrier, excipient, or diluent. The disclosed particles may be used for preparing a pharmaceutical composition for modulating expression of one or more genes in a patient in need thereof. In some embodiments, the disclosed particles are used for preparing a pharmaceutical composition for treating cancer in a patient in need thereof, which may include but is not limited to breast cancer. In further embodiments, the cancer may be refractory or resistant to treatment with a chemotherapeutic agent.

Also contemplated herein are kits that include a pharmaceutical composition comprising the presently disclosed particles and further including a pharmaceutical composition comprising a chemotherapeutic agent. Suitable chemotherapeutic agents for the kits may include, but are not limited to doxyorubicin liposomal.

The presently disclosed particles may be utilized in methods for modulating expression of a gene in a cell (e.g., inhibiting expression of the gene in the cell via promoting degradation of mRNA for the gene). The methods may be performed in vitro or in vivo. The contemplated methods may include methods for inhibiting expression of a gene in a cell, the methods including contacting the cell with the presently disclosed particles where the particles bind specifically to the cell and the particles include an siRNA that inhibits expression of the gene.

The presently disclosed particles may be utilized in methods for treating or preventing a disease or disorder in patient in need thereof. For example, the disclosed particles may be formulated as a pharmaceutical composition for treating or preventing cancer or a proliferative disorder in a patient in need thereof. The pharmaceutical compositions comprising the disclosed particles may be administered to a patient in a treatment regimen with a chemotherapeutic agent, which may be administered to the patient prior, concurrently with, or after the pharmaceutical compositions comprising the disclosed particles are administered to the patient.

Also contemplated herein are methods of making the disclosed particles. In some embodiments, the methods include the following steps: (a) obtaining bacteriophage comprising or consisting of a plurality of fusion proteins displaying a binding peptide for a desired target site (e.g., landscape bacteriophage); (b) treating the bacteriophage with a denaturing agent; (c) isolating or purifying the phage fusion protein from the treating bacteriophage (e.g., removing phage DNA and other components); (d) preparing a mixture of the isolated or purified phage fusion protein and heterologous nucleic acid to form the targeted particle; and (e) isolating or purifying the targeted particle from the mixture. Suitable denaturing agents include detergents. Typically, the targeted particles are formed from a mixture that comprises a molar excess of fusion proteins relative to nucleic acid. In other embodiments, the disclosed particles may be prepared by: (a) preparing a mixture of (i) a solution of isolated or purified landscape phage fusion proteins and (ii) a solution of isolated or purified heterologous nucleic acid where the targeted particle forms in the mixture; and (b) isolating or purifying the targeted particle from the mixture.

BRIEF DESCRIPTION OF THE DRAWINGS

FIG. 11. Analysis of GAPDH protein expression in MCF-7 or MCF-10A cells by Western blot. (A). Relative level of protein synthesis in cells treated with: 1. VEEGGYIAA phage-siRNA complex in MCF-7 cells; 2. control VEEGGYIAA phage-NesiRNA in MCF-7 cells; 3. Control non-treated MCF7-cells, 4. VEEGGYIAA phage-siRNA complex in MCF-10A cells; 5. Control non-treated MCF10A-cells. (B). Western blot band intensities quantified using Image J software (NIH). All data represent the mean±S. D.*P<0.05, student-t-test.

DETAILED DESCRIPTION

Figure 1:
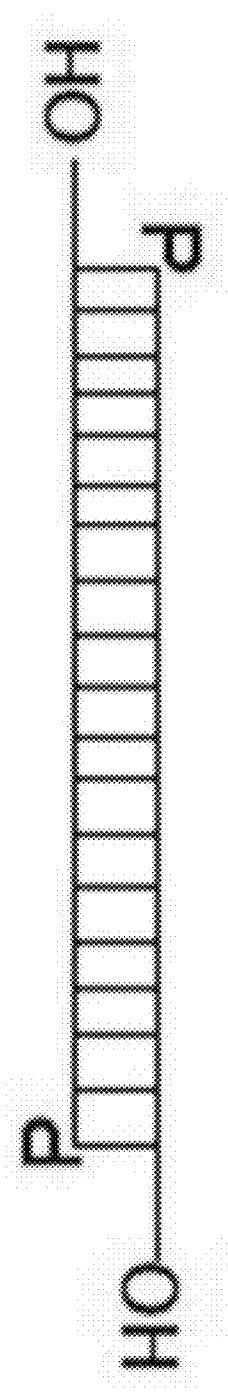
FIG. 1. is a schematic representation of an siRNA molecule: a ~19-21 basepair RNA core duplex that is followed by a 2 nucleotide 3' overhang on each strand. OH: 3' hydroxyl; P: 5' phosphate.

The present invention is described herein using several definitions, as set forth below and throughout the application.

Unless otherwise specified or indicated by context, the terms "a", "an", and "the" mean "one or more." For example, "a targeted particle" should be interpreted to mean "one or more targeted particles."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." For example, a "pharmaceutical composition that includes a targeted particle" should be interpreted to mean "a pharmaceutical composition that comprises a targeted particle."

In some embodiments, the targeted particles disclosed herein may have one or more dimensions (e.g., dimensions such as length and/or effective diameter) that are between about 1 nm and 1000 nm. As such, the targeted particles may be referred to as "targeted nanoparticles."

The targeted particles disclosed herein typically include a plurality of landscape phage fusion proteins. Although the term "plurality" should be interpreted to mean more than one, typically, herein the term "plurality" means several hundred or thousand (e.g., at least about 100, 200, 300, 400, 500, 1000, 2000, 3000, or 4000).

Suitable landscape phage fusion proteins for the targeted particles disclosed herein may include pVIII major coat protein either in precursor or mature form, or mutants, variants, or fragments thereof. As used herein, "pVIII" refers to the major coat protein of the filamentous phage f1, fd, and M13 that belong to the Ff family. The completed coding sequence of a filamentous phage display vector f8-1 is deposited at GenBank under accession number AF218734.1 and encodes a major coat protein pVIII mutant precursor having an amino acid sequence MKKSLVLKASVAVATLVPMLSFAAE-GEDPAKAAFDSLQASATEYIGYAWAMVV VIVGA-TIGIKLFKKFTSKAS (SEQ ID NO:1). The complete coding sequence of a filamentous phage display vector f8-5 is deposited at GenBank under accession number AF464138.1 and major coat protein pVIII precursor also having an amino acid sequence MKKSLVLKASVAVATLVPMLSFAAEGED-PAKAAFDSLQASATEYIGYAWAMVV VIVGA-TIGIKLFKKFTSKAS (SEQ ID NO:1). The vector f8-5 was constructed by engineering several single-base-pair substitutions into filamentous phage cloning vector f8-1 and is intended as a phage-display vector. The vector 18-5 has PstI, BamHI, NheI and MluI cloning sites in gene VIII and confers tetracycline resistance to the host *Escherichia coli* cells. 'Stiffers' between these cloning sites can be replaced with degenerate coding sequences to create libraries of phage displaying different random peptides in exposed area of all 4000 copies of the major coat protein pVIII. The vector f8-5 then may be utilized to create a phage library which may be screened as described herein to isolate phage that bind specifically to a target.

The presently disclosed particles, compositions, kits, and methods contain and/or utilize a plurality of landscape phage fusion proteins complexed with heterologous nucleic acid, the landscape phage fusion proteins displaying a heterologous peptide and the targeted particle binding specifically to a target site. As utilized herein, a protein, polypeptide, and peptide refer to a molecule comprising a chain of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terms "protein," "polypeptide," and "peptide" may be referred to interchangeably herein. However, the terms may be distinguished as follows. A "protein" typically refers to the end product of transcription, translation, and post-translation modifications in a cell. Accordingly, a protein typically exhibits a biological function. A polypeptide is typically an amino acid chain of length ≥50 amino acids (Garrett & Grisham, Biochemistry, $2^{nd}$ edition, 1999, Brooks/Cole, 110, which is incorporated herein by reference in its entirety). A polypeptide, as contemplated herein, may comprise, but is not limited to, 50, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. A peptide, in contrast to a polypeptide, typically is a short polymer of amino acids, of a length typically of 20 or less amino acids (Garrett & Grisham, Biochemistry, $2^{nd}$ edition, 1999, Brooks/Cole, 110, which is incorporated herein by reference in its entirety). In some embodiments, a peptide as contemplated herein may include no more than about 8, 9, 10, 11, 12, 13, 14, 15, 16, 17, 18, 19, or 20 amino acids.

As contemplated herein, "a mutant or variant" of a reference protein, polypeptide, or peptide, typically has an amino acid sequence that is at least about 50% identical (preferably at least about 60%, 70%, 80%, 90%, 95%, 96%, 97%, 98%, or 99% identical) to the reference protein, polypeptide, or peptide. For example, a mutant or variant of the major coat protein pVIII typically has an amino acid sequence that is at least about 50%, 60%, 70%, 80%, 90%, 95%, 96%, 97%, 98%, or 99% identical to the amino acid sequence of major coat protein pVIII. Preferably, the mutant or variant retains at least one or more biological functions of the reference protein, polypeptide, or peptide. For example, where the reference protein is the major coat protein pVIII, preferably a mutant or variant thereof retains at least one biological function of the major coat protein pVIII precursor such as the biological function of binding to nucleic acid and/or the biological function of assembling into a higher order phage particle.

The landscape phage fusion protein of the presently disclosed targeted particles displays a heterologous peptide. As used herein, "heterologous peptide" may be interpreted to mean a peptide inserted into a landscape phage protein to provide the landscape phage fusion protein having an inserted amino acid sequence with respect to the landscape phage protein. A "heterologous peptide" may have an artificial amino acid sequence or a naturally occurring amino acid sequence not normally present in the landscape phage protein. As used herein, a "heterologous peptide" may refer to a "guest peptide."

Nucleic acid as contemplated herein includes ribonucleic acid (RNA) and deoxyribonucleic acid (DNA) which may be single- or double-stranded (i.e., ssRNA, ssDNA, dsRNA, dsDNA). Double stranded nucleic acid may be fully or partially double-stranded and may include single-stranded overhangs at one or both ends of the nucleic acid molecule. RNA may include small inhibitory ribonucleic acid (siRNA).

In the disclosed particles, the nucleic acid complexed with the landscape phage fusion proteins may be heterologous. As used herein, "heterologous nucleic acid" may be interpreted to mean non-phage nucleic acid. A heterologous nucleic acid with respect to the landscape phage fusion proteins may be interpreted to mean a nucleic acid having a nucleic acid sequence derived from a species other than the phage from which the landscape phage proteins are derived or a nucleic acid having a nucleic acid sequence not present in the phage genome from which the landscape phage protein are derived. In addition, a "heterologous nucleic acid" may have an artificial nucleic acid sequence or a naturally occurring nucleic acid sequence not normally present in the phage genome from which the landscape phage protein.

A "fragment" of a protein or a polypeptide as contemplated herein refers to a contiguous portion of the amino acid sequence of the protein or polypeptide. A fragment of a protein or polypeptide refers to less than a full-length amino acid sequence of the protein or polypeptide (e.g., where the full-length amino acid sequence is truncated at the N-terminus, the C-terminus, or both termini). For example, a fragment of a protein or polypeptide may comprise or consist of a 5-200, 5-150, 5-100, 5-50, 5-25, 5-15, 10-200, 10-150, 10-100, 10-50, 10-25, or 10-15 contiguous amino acid sequence of the full-length protein or polypeptide. The major coat protein pVIII may be expressed as a precursor which subsequently is processed to provide a fragment of the precursor. For example, the major coat protein pVIII precursor may have a sequence MKKSLVLKASVAVATLVPMLSFAAEGEDPAKAAFDSLQASATEYIGYAWAMVVVIVGATIGIKLFKKFTSKAS (SEQ ID NO: 1) which subsequently is processed at its N-terminus to remove a 23 amino acid leader sequence and provide a mature fragment having an amino acid sequence AEGEDPAKAAFDSLQASATEYIGYAWAMVVVIVGATIGIKLFKKFTSKAS (SEQ ID NO:2). Mutants or variants of the mature fragment of major coat protein pVIII precursor may have an amino acid sequence AXXXXXXXXDPAKAAFDSLQASATEYIGYAWAMVVVIVGATIGIKLFKKFTSKAS (SEQ ID NO:3), where amino acids 2-4 of SEQ ID NO:2 are replaced by a peptide have a random amino acid sequence that is 8 residues in length (i.e., $X_8$). Mutants or variants of the mature fragment of major coat protein pVIII precursor may have an amino acid sequence AXXXXXXXXXPAKAAFDSLQASATEYIGYAWAMVVVIVGATIGIKLFKKFTSKAS (SEQ ID NO:4), where amino acids 2-5 of SEQ ID NO:2 are replaced by a peptide have a random amino acid sequence that is 9 residues in length (i.e., $X_9$).

The targeted particles disclosed herein may include heterologous nucleic acid that is relatively small in size. For example, in some embodiments the heterologous nucleic acid has a nucleic acid sequence that is about 10-50 nucleotides in length (or about 15-30 nucleotides in length, or about 20-25 nucleotides in length). The nucleic acid may be partially or fully double-stranded and may include single-stranded overhangs at one or both ends of the nucleic acid molecule. The targeted particles may include one type of heterologous nucleic acid (i.e., a single type of nucleic acid molecule) or may include a plurality of different types of heterologous nucleic acid. For example, the targeted particles may include a mixture of different RNA and/or DNA molecules (e.g., a mixture of different siRNAs). Where the targeted particles include a mixture of different nucleic acid molecules, "size" may be determined as "average size," in which case, the heterologous nucleic acid may have a nucleic acid sequence that is about, on average, 10-50 nucleotides in length (or about 15-30 nucleotides in length, or about 20-25 nucleotides in length).

In some embodiments, the targeted particles disclosed herein may include a plurality of small interfering RNA (siRNA) molecules which may be the same or different. Small interfering RNA (siRNA) is a class of double-stranded RNA (dsRNA) molecules, typically 20-25 nucleotides (nt) in length that are involved in the RNA interference (RNAi) pathway, where it interferes with the expression of a specific gene (e.g., by inducing degradation of mRNA associated with the gene). The structure of siRNAs typically is a dsRNA molecule typically about 19-21 nt in length with 2-nt 3' overhangs on either end. (See FIG. 1). Each strand of the dsRNA has a 5' phosphate group and a 3' hydroxyl group, the result of processing by dicer, an enzyme that converts long dsRNAs or small hairpin RNAs into siRNAs. siRNAs can be transfected into cells by various methods to bring about the specific knockdown of a gene of interest. Generally, any gene whose sequence is known can, thus, be targeted based on sequence complementarity with an appropriately tailored siRNA.

The targeted particles disclosed herein may include siRNA that is targeted to a gene selected from the genes listed in Table 1 which discloses a representative list of genes associated with cancer or associated with resistance to chemotherapeutic treatment of cancer (e.g., drug resistance genes such as PARP-1, MDR1/Pgp, MRP1, and BRCP). For example, the siRNA may modulate the expression of one or more genes listed in Table 1. As used herein, "modulating expression" should be interpreted to mean inhibiting expression or increasing expression. Typically, the siRNA present in the disclosed particles inhibits expression of one or more genes listed in Table 1.

The disclosed particles may be prepared by a method that includes (a) obtaining bacteriophage comprising a plurality of fusion proteins displaying a binding peptide for a desired target site; (b) treating the bacteriophage with a denaturing agent (e.g., a detergent which may include an ionic detergent); (c) preparing a mixture of the treated bacteriophage and heterologous nucleic acid to form the targeted particle; and (d) isolating or purifying the targeted particle from the mixture (e.g., via centrifugation and/or a separation method such as filtration chromatography which may include high pressure liquid chromatography (HPLC)). Typically, the targeted particles are formed from a mixture that comprises a molar excess of fusion proteins relative to nucleic acid (e.g., at least a 10, 20, 30, 40, 50, 60, 70, 80, 90, or 100-fold molar excess). In some embodiments, the targeted particles are formed from a mixture that comprises a 10-80 molar excess of fusion proteins relative to nucleic acid. In other embodiments, the disclosed particles may be prepared by a method that includes: (a) preparing an mixture of (i) a solution of isolated or purified landscape phage fusion proteins (e.g., non-assembled landscape phage fusion proteins or disassembled landscape fusion proteins) and (ii) a solution of isolated or purified heterologous nucleic acid where the targeted particle forms in the mixture; and (b) isolating or purifying the targeted particle from the mixture. In the methods of preparing the targeted particles, the landscape phage fusion proteins may be obtained from recombinant phage or from other recombinant expression systems. Alternatively, the landscape phage fusion proteins may be chemically synthesized. In the methods of preparing the targeted particles, the heterologous nucleic acid may be obtained from recombinant expression systems. Alternatively, the heterologous nucleic may be chemically synthesized.

Proteins, polypeptides, peptides, and nucleic acid may be synthesized by any technique known to those of skill in the art, including the expression of proteins, polypeptides, peptides, and nucleic acid through standard molecular biological techniques, the isolation of proteins, polypeptides, peptides, and nucleic acid from natural sources, or the chemical synthesis of proteins, polypeptides, peptides, or nucleic acid. For example, proteins, polypeptides, peptides may be prepared using synthetic organic chemistry methods, such as solid phase synthesis where an amino acid's carboxylic acid is activated for amide bond formation with dicyclohexyl carbodiimide (Garrett & Grisham, Biochemistry, $2^{nd}$ edition, 1999, Brooks/Cole, 150).

Proteins, polypeptides, and peptides as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

As used herein, the terms "isolated" or "purified" mean removed from a natural source and/or separated from natural or other components. For example, a solution of an isolated or purified landscape phage fusion protein means a solution comprising a landscape phage fusion protein that is removed from a natural source (e.g., recombinant phage) and/or separated from natural or other components. A solution of an isolated or purified landscape phage fusion protein may be interpreted to mean a solution in which the landscape phage fusion protein represents at least about 90% (w/w) of the solubilized or protein components in the solution (preferably at least about 95%, 96%, 97%, 98%, or 99% of the solubilized or protein components in the solution). A solution of an isolated or purified landscape phage fusion protein may be interpreted to mean a solution in which the landscape phage fusion protein represents at least about 90% (w/w) of the solute of the solution (preferably at least about 95%, 96%, 97%, 98%, or 99% of the solute of the solution). Similarly, a solution of an isolated or purified nucleic acid may be interpreted to mean a solution in which the nucleic acid represents at least about 90% (w/w) of the solubilized or nucleic acid components in the solution (preferably at least about 95%, 96%, 97%, 98%, or 99% of the solubilized or nucleic acid components in the solution). A solution of an isolated or purified nucleic acid may be interpreted to mean a solution wherein the nucleic acid represents at least about 90% (w/w) of the solute of the solution (preferably at least about 95%, 96%, 97%, 98%, or 99% of the solution).

The targeted particles comprise or consist of a plurality of landscape phage fusion proteins complexed with heterologous nucleic acid. The landscape phage fusion protein and the heterologous nucleic acid may represent the sole components of the targeted particles. As such, the targeted particles may consist of the plurality of landscape phage fusion proteins complexed with heterologous nucleic acid. In some embodiments, the landscape phage fusion proteins complexed with heterologous nucleic acid together represent the major components of the targeted particles. For example, the landscape phage fusion proteins complexed with heterologous nucleic acid together may represent at least about 50% (w/w) of the targeted particles (or at least 60%, 70%, 80%, 90%, 95%, 96%, 97%, 98%, or 99% (w/w) of the targeted particles.

Surprisingly, the disclosed targeted particles can bind to a targeted cell and be taken into the cell without the targeted particles comprising liposomal or micelle components. As such, the disclosed targeted particles may be prepared without liposomal or micelle components and need not include liposomal or micelle components. For example, in some embodiments the disclosed targeted particles do not include amphipathic lipid molecules such as phospholipids. For example, the targeted particles may comprise no more than 5% (w/w) phospholipids (or no more than 4%, 3%, 2%, or 1% (w/w) phospholipids).

The presently disclosed particles may be formulated in pharmaceutical compositions that comprise an "effective amount" of the particles as a therapeutic agent. As used herein, the phrase "effective amount" shall mean that dosage that provides the specific pharmacological response for which the agent is administered in a significant number of patients in need of such treatment. An effective amount of an agent that is administered to a particular patient in a particular instance will not always be effective in treating the conditions/diseases described herein, even though such dosage is deemed to be a therapeutically effective amount by those of skill in the art.

As used herein, a "patient" may be interchangeable with "subject" and means an animal, which may be a human or non-human animal, in need of treatment. Non-human animals may include dogs, cats, horses, cows, pigs, sheep, and the like.

A "patient in need thereof" may include a patient having or at risk for developing a cell proliferative disease or disorder. A patient having or at risk for developing a cell proliferative disease or disorder, such as cancer, may include a patient having or at risk for developing Acute Lymphoblastic Leukemia (ALL), Acute Myeloid Leukemia (AML), Adrenocortical Carcinoma, AIDS-Related Cancers such as Kaposi Sarcoma and Lymphoma, Anal Cancer, Appendix Cancer, Astrocytomas, Atypical Teratoid/Rhabdoid Tumor, Childhood, Central Nervous System, Basal Cell Carcinoma, Bile Duct Cancer such as Extrahepatic Bile Duct Cancer, Bladder Cancer, Bone Cancer such as Osteosarcoma and Malignant Fibrous Histiocytoma, Brain Stem Glioma, Brain-Related Tumors (e.g., Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, and Supratentorial Primitive Neuroectodermal Tumors and Pineoblastoma), Breast Cancer (e.g., female or male), Bronchial Tumors, Burkitt Lymphoma (i.e., Non-Hodgkin Lymphoma), Carcinoid Tumor such as Gastrointestinal Carcinoid Tumors, Central Nervous System (CNS)-Related Tumors (e.g., Atypical Teratoid/Rhabdoid Tumors, Embryonal Tumors, and Primary Lymphomas of the CNS), Cervical Cancer, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (e.g., Mycosis Fungoides and Sézary Syndrome), Ductal Carcinoma In Situ (DCIS), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Eye Cancer (e.g., Intraocular Melanoma and Retinoblastoma), Gallbladder Cancer, Gastric (Stomach) Cancer, Gastrointestinal Stromal Tumors (GIST), Germ Cell Tumor (e.g., Extracranial, Extragonadal, and Ovarian Tumors), Gestational Trophoblastic Tumor, Hairy Cell Leukemia, Head and Neck Cancer, Heart Cancer, Hepatocellular (Liver) Cancer, Histiocytosis such as Langerhans Cell Histiocytosis, Hodgkin Lymphoma, Hypopharyngeal Cancer, Islet Cell Tumors (Endocrine Pancreas), Kidney Cancer (e.g., Renal Cell Cancer), Laryngeal Cancer, Lip and Oral Cavity Cancer, Lobular Carcinoma In Situ (LCIS), Lung Cancer (e.g., Non-Small Cell Lung Cancer or Small Cell Lung Cancer), Macroglobulinemia (e.g., Waldenström Macroglobulinemia, Medulloblastoma, Medulloepithelioma, Melanoma, Merkel Cell Carcinoma, Malignant Mesothelioma, Metastatic Squamous Neck Cancer with Occult Primary, Mouth Cancer, Multiple Endocrine Neoplasia Syndromes, Multiple Myeloma/Plasma Cell Neoplasm, Myelodysplastic Syndromes, Myelodysplastic/Myeloproliferative Neoplasms, Nasal Cavity and Paranasal Sinus Cancer, Nasopharyngeal Cancer, Neuroblastoma, Oral Cancer, Oropharyngeal Cancer, Ovarian Cancer (e.g., Epithelial, Germ Cell Tumor, and Low Malignant Potential Tumor), Pancreatic Cancer (e.g., Islet Cell Tumors), Papillomatosis, Paraganglioma, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Childhood, Prostate Cancer, Rectal Cancer, Renal Pelvis and Ureter Transitional Cell Cancer, Respiratory Tract Cancer with Chromosome 15 Changes, Rhabdomyosarcoma, Salivary Gland Cancer, Skin Cancer, Small Intestine Cancer, Squamous Cell Carcinoma, Stomach (Gastric) Cancer, Supratentorial Primitive Neuroectodermal Tumors, Testicular Cancer, Throat Cancer, Thymoma and Thymic Carcinoma, Thyroid Cancer, Trophoblastic Tumor, Urethral Cancer, Uterine Cancer (Endometrial), Uterine Sarcoma, Vaginal Cancer, Vulvar Cancer, or Wilms Tumor. In some embodiments, the patient has or is at risk for developing breast cancer.

As contemplated herein, a patient may include a patient having or at risk for developing cancer and who has been administered a chemotherapeutic agent. Chemotherapeutic agents may include agents selected from a group consisting of F13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortefg, Deltasone®, Denileukin Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin Ixabepilone Ixempra™, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa®. In some embodiments, the patient is refractory.

The presently disclosed particles formulated as pharmaceutical compositions may be administered to a patient in need thereof together with a chemotherapeutic agent. The chemotherapeutic agent may have been administered to the patient prior to when the pharmaceutical compositions comprising the disclosed particles are administered to the patient.

In other embodiments, the chemotherapeutic agent is administered to the patient concurrently or after the pharmaceutical compositions comprising the disclosed particles are administered to the patient.

The targeted particles utilized in the methods disclosed herein may be formulated as pharmaceutical compositions that include: (a) a therapeutically effective amount of the targeted particles as disclosed herein; and (b) one or more pharmaceutically acceptable carriers, excipients, or diluents. The pharmaceutical compositions may be administered prophylactically or therapeutically. In prophylactic administration, the compositions may be administered in an amount sufficient to induce a response for protecting against disease. In therapeutic applications, the compositions are administered to a patient in an amount sufficient to elicit a therapeutic effect (e.g., a response which cures or at least partially arrests or slows symptoms and/or complications of disease (i.e., a "therapeutically effective dose")).

The pharmaceutical composition disclosed herein may be delivered via a variety of routes. However, typical delivery routes involve parental administration (e.g., intravenous, intradermal, intramuscular or subcutaneous delivery). Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical compositions may include a carrier. For example, the carrier may be selected from the group consisting of proteins, carbohydrates, sugar, talc, magnesium stearate, cellulose, calcium carbonate, and starch-gelatin paste.

The pharmaceutical compositions may include a diluent. Suitable diluents may include pharmaceutically acceptable aqueous and non-aqueous sterile injection solutions, inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

The pharmaceutical compositions may include an excipient. Suitable excipients include lightly crosslinked polyvinyl pyrrolidone, corn starch, potato starch, maize starch, and modified starches, croscarmellose sodium, cross-povidone, sodium starch glycolate, and mixtures thereof.

EXAMPLES

The following Examples are illustrative and are not intended to limit the scope of the claimed subject matter.

Example 1

Targeted Delivery of siRNA Via Phage Fusion Protein

Abstract

RNA interference (RNAi) holds considerable promise as a therapeutic approach to silence disease-causing genes. The primary obstacles in achieving the addressed delivery of small interfering RNA (siRNA) in vivo include, non-competitive cells uptake by non-target cells, degradation by nucleases and endosomal trapping. A new challenge in the targeted delivery of siRNA, is development of highly selective, stable, active and physiologically acceptable ligands that would navigate the encapsulated drugs to the site of the disease and control their unloading inside the cancer cells. Here, a nanotechnological platform for breast tumor-targeted siRNA delivery is proposed. This platform utilizes the unique propensity of phage proteins to self-assemble in the presence of nucleic acids and to form particles mimicking the structure of the phage capsid.

Introduction

Figure 2:
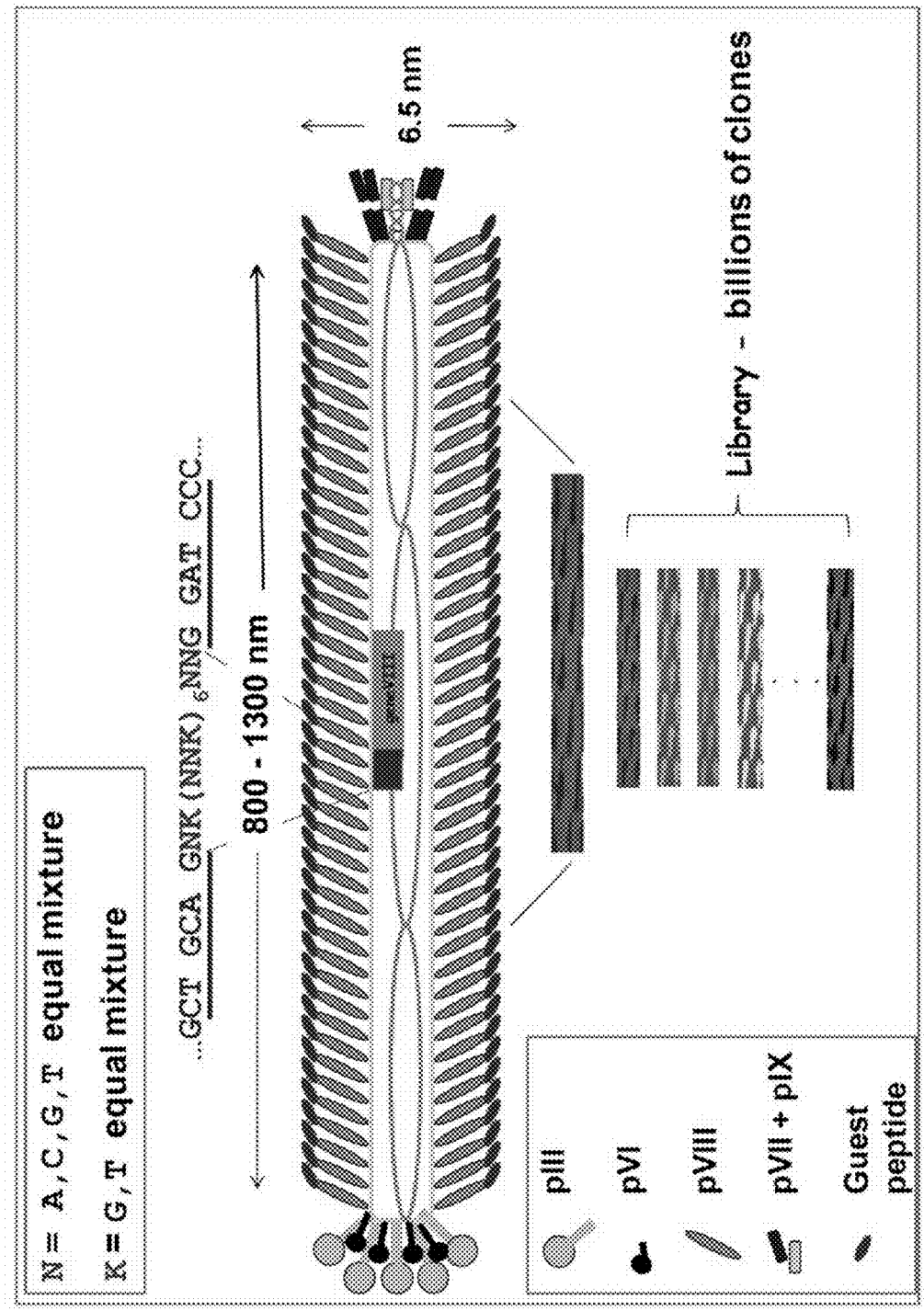
FIG. 2. illustrates a recombinant phage particle library formed from pVIII fusion proteins that display a "guest peptide."
Figure 3:
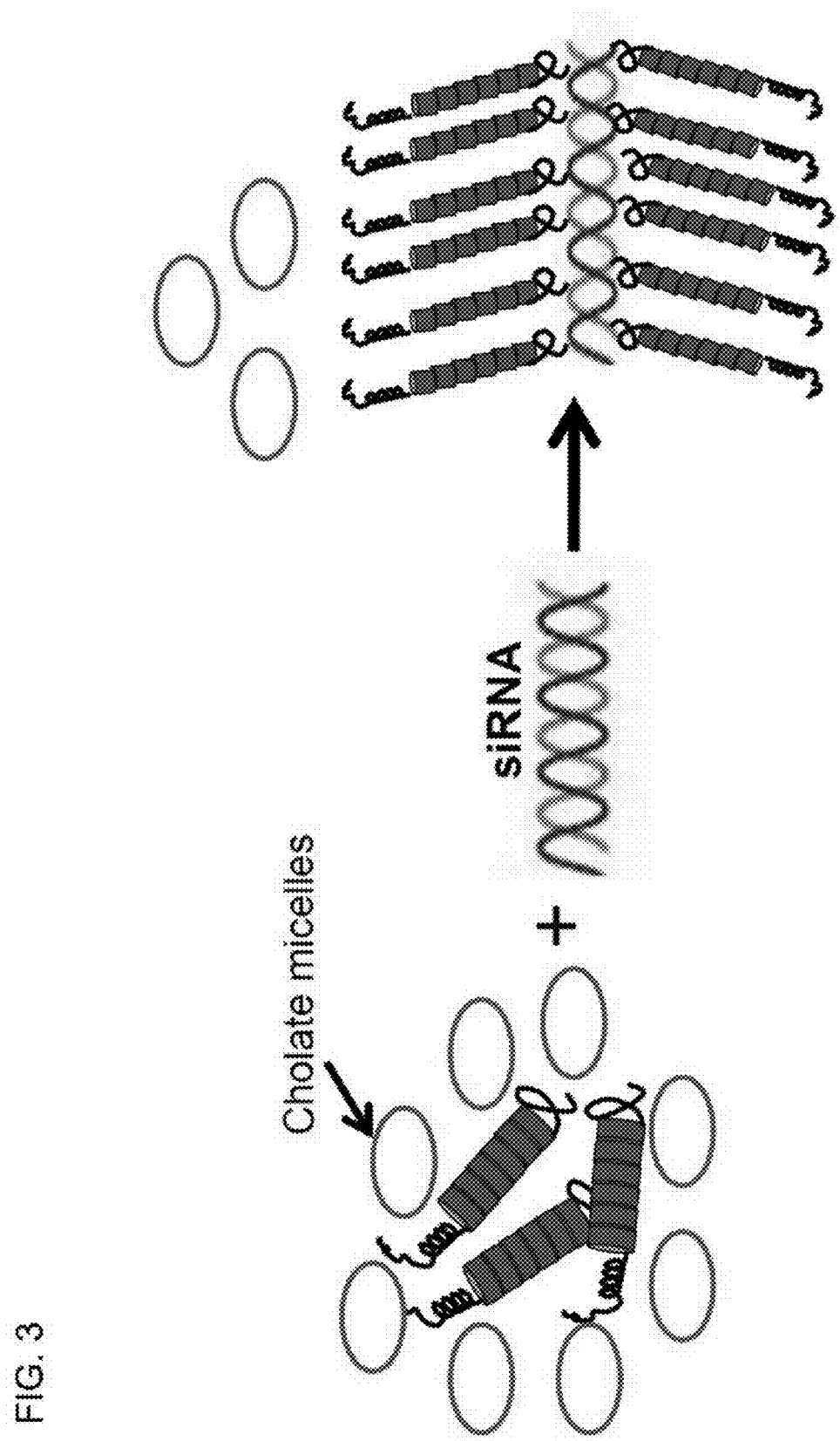
FIG. 3. illustrates that the selected tumor-specific phage can be converted into the siRNA-phage protein complex by their self-assembly, resembling phages.
Figure 4:
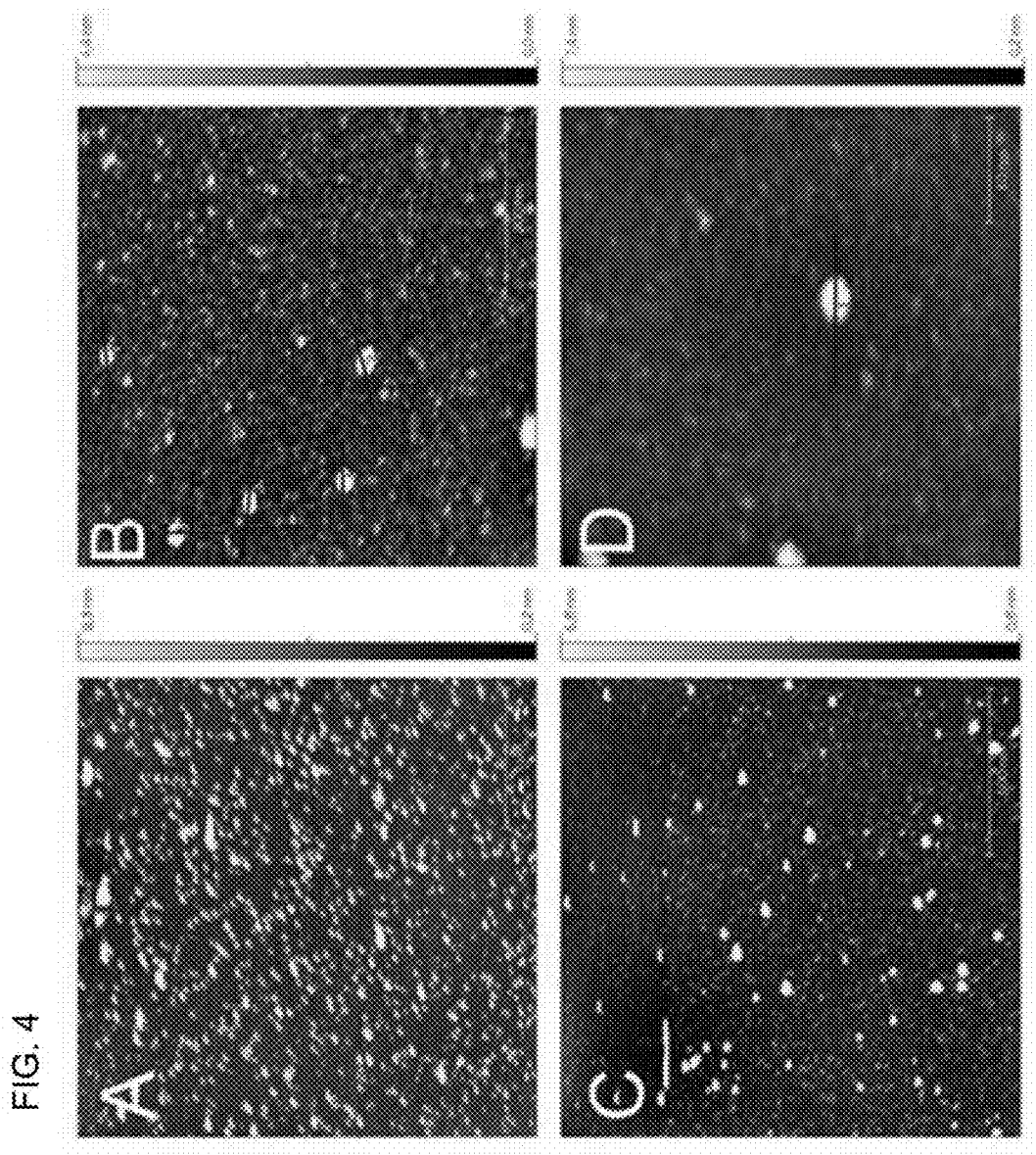
FIG. 4. atomic force microscopy analysis illustrating a dense layer of siRNA-nanophage complexes (scan size: A=3 µm, B=500 nm, C=1.5 µm, D=250 nm). The cross sections belong to image B and D.

Selective oncogene silencing, mediated by siRNA shows promise for cancer treatment. However, the obstacles in successfully delivering siRNA hinder the therapeutic viability of this treatment. Various viral and non-viral methods are used to overcome the challenge of delivery of siRNA into the cells including liposomes[9], cell penetrating peptides[4,5] and cell-targeting ligands. Phage display has emerged as a robust technology for identifying cell-targeting ligands[10]. Here, landscape phage display is proposed to provide a source of targeting ligands. The major principle of the proposed innovative idea is that the gene silencing siRNAs are encapsulated into targeted phage proteins that protect them against degradation and deliver to the receptors, cells, tissues and organs that have been used for selection of the precisely targeting phage. The tumor-specific peptides genetically fused to all 4,000 copies of the phage's major coat protein pVIII[6] have been affinity selected from multibillion clone libraries (see FIG. 2) by their ability to bind very specifically cancer cells, penetrate into the cells or accumulate in the tumor-surrounding vasculature. The landscape phage fusion proteins can be isolated from these phage, mixed with siRNA such that the landscape phage fusion proteins and siRNA self-assemble into phage-like particles. (See FIGS. 3-5). In FIG. 4, the diameter of the single complex is larger than the determined values because of the tip broadening effect. The presence of a dense layer was confirmed with nanolithography experiments (not shown). In FIG. 4, single siRNA-nanophage complexes can be seen beside the scratched hole (left and right). The holes on the surrounding area are defects in the APTES layer.

Experimental Methods and Results

Landscape Phage Clones for Breast Cancer Cells

Figure 6:
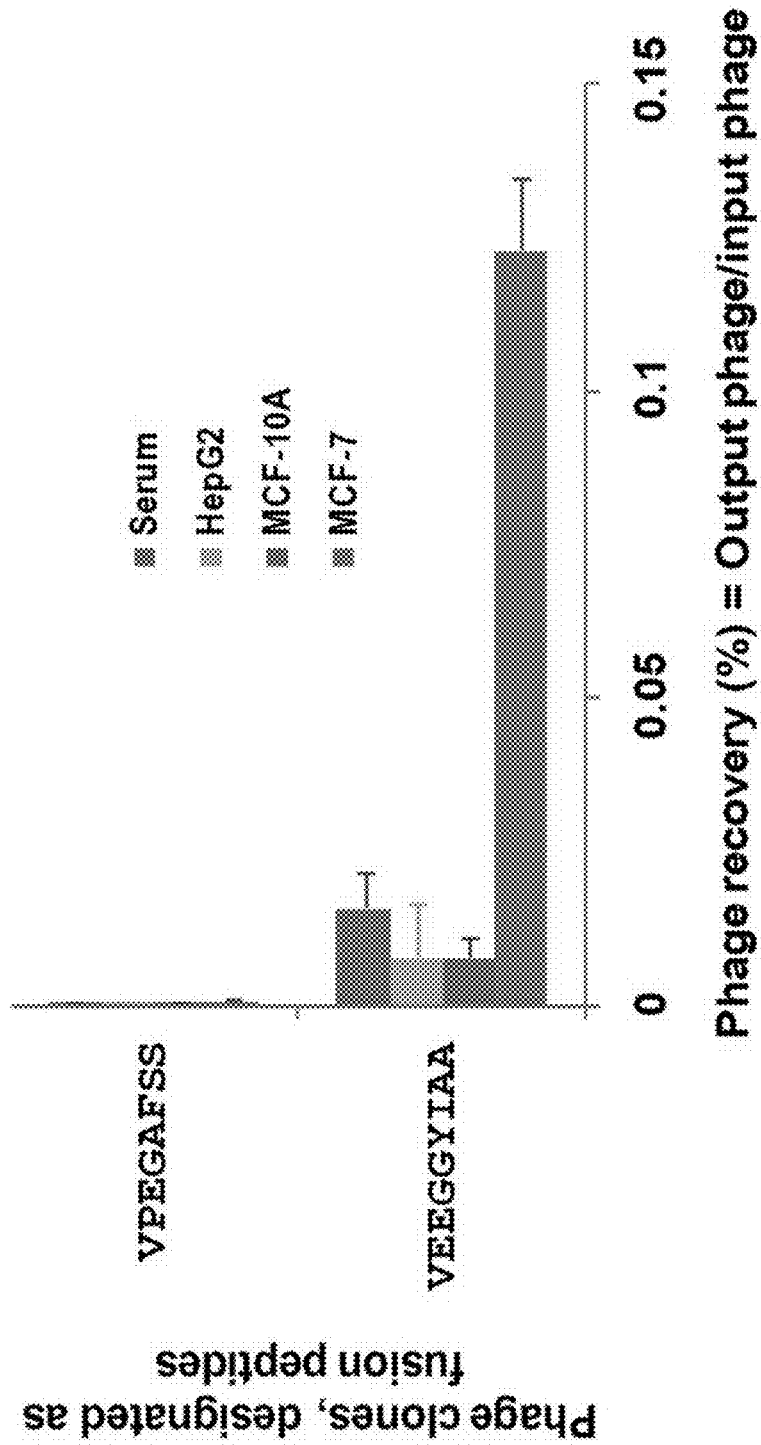
FIG. 6. illustrates selectivity of phage VEEGGYIAA (SEQ ID NO:7) towards breast cancer cells MCF-7 in comparison with normal breast cells MCF-10A and hepatocellularcarcinoma HepG2. Unrelated phage bearing the peptide VPEGAFSS (SEQ ID NO:8) was used as a control.

Highly selective and specific landscape phage ligands for human breast carcinoma cells MCF-7 and ZR-75-1 were selected using landscape phage libraries f8/8 and f8/9[10,21] (also see Example 2 below) and earlier developed biopanning procedure[14]. Individual phage clones identified by DNA sequencing were propagated, purified and tested for binding with target MCF-7 or ZR-75-1 cells in comparison with control normal epithelial cells MCF-10A and hepatocellular carcinoma cells HepG2 (FIG. 6). Phage harboring peptide VEEGGYIAA (SEQ ID NO:7) was identified as being one of the most selective binders to MCF-7 cells, which was also able to penetrate into the cells. Control phage bearing the unrelated peptide VPEGAFSS (SEQ ID NO:8) and the "wildtype" vector phage f8-5 demonstrated negligible binding to cells.

siRNAs Targeted to MCF-7 Cells by Phage Protein.

Figure 7:
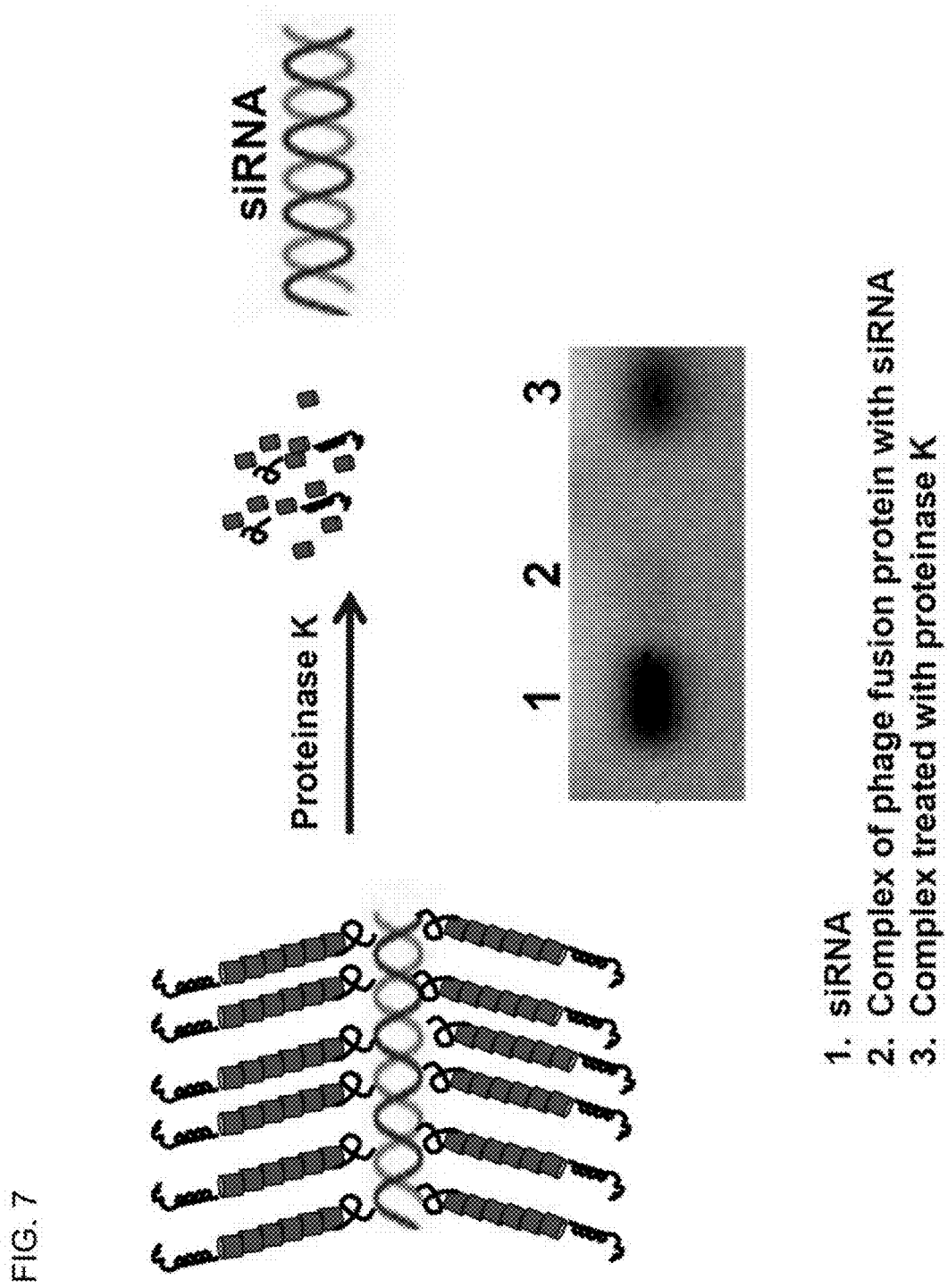
FIG. 7. illustrates the analysis of the complex of siRNA with phage protein. The complex was analyzed by gel-electrophoresis (1% agarose, SIBR green). 1: siRNA control; 2: phage protein-siRNA (molar ratio 80:1), 3: Proteinase K-mediated release of siRNA from protein-siRNA complex.
Figure 8:
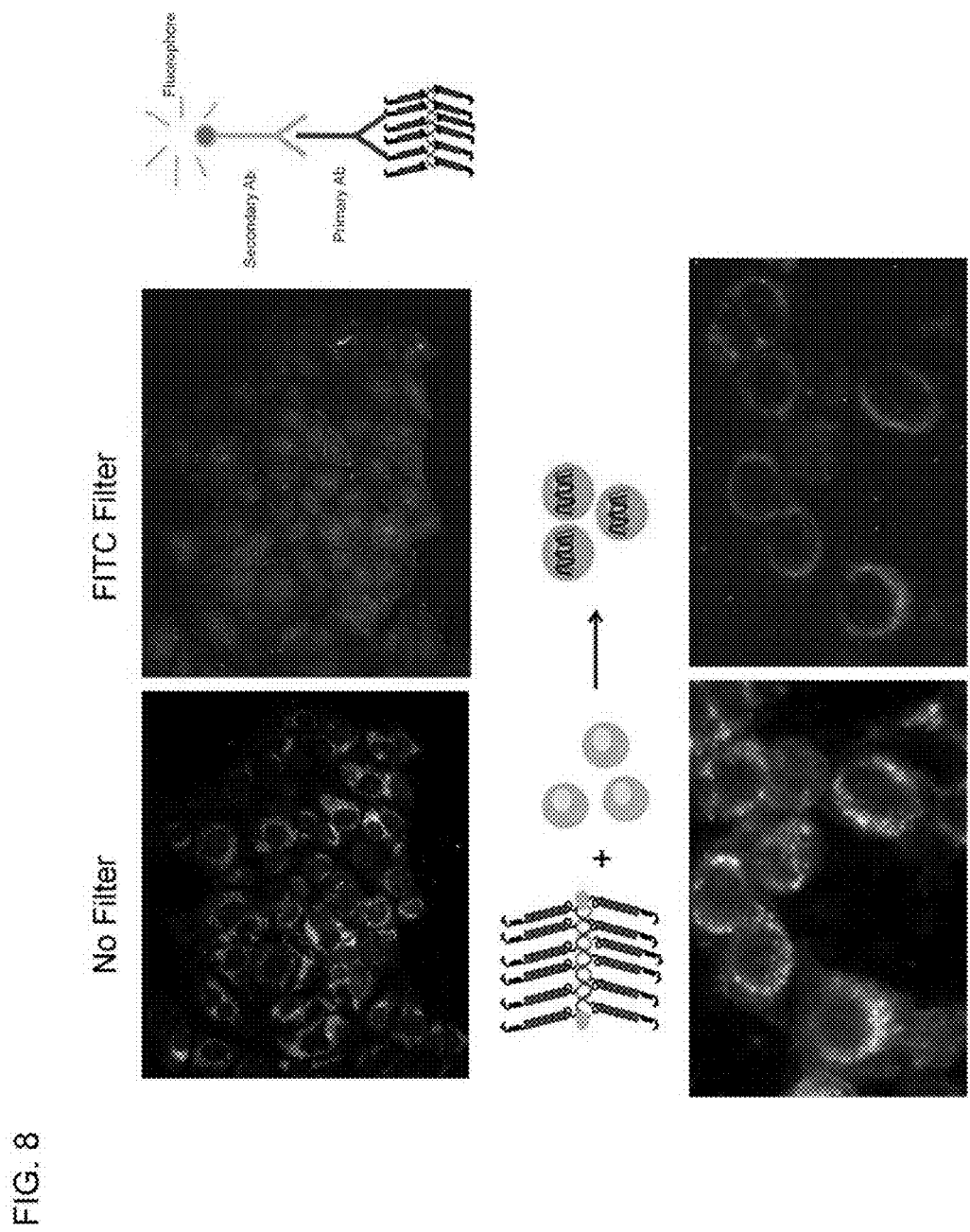
FIG. 8. illustrates the cellular localization of phage-siRNA complex inside MCF-7 cells by fluorescence microscopy. Cells incubated with protein-siRNA complex (80:1) for 24 hrs were fixed, permeabilized, stained with anti-fd phage antibody followed by Alexa fluor 488 goat anti rabbit antibody (Upper, left (no filter), right (FITC filter), or incubated with protein-Alexa fluor 488-labelled siRNA for 24 hours and were trypsinized washed and viewed (Lower, left (no filter), right (FITC-filter).
Figure 9:
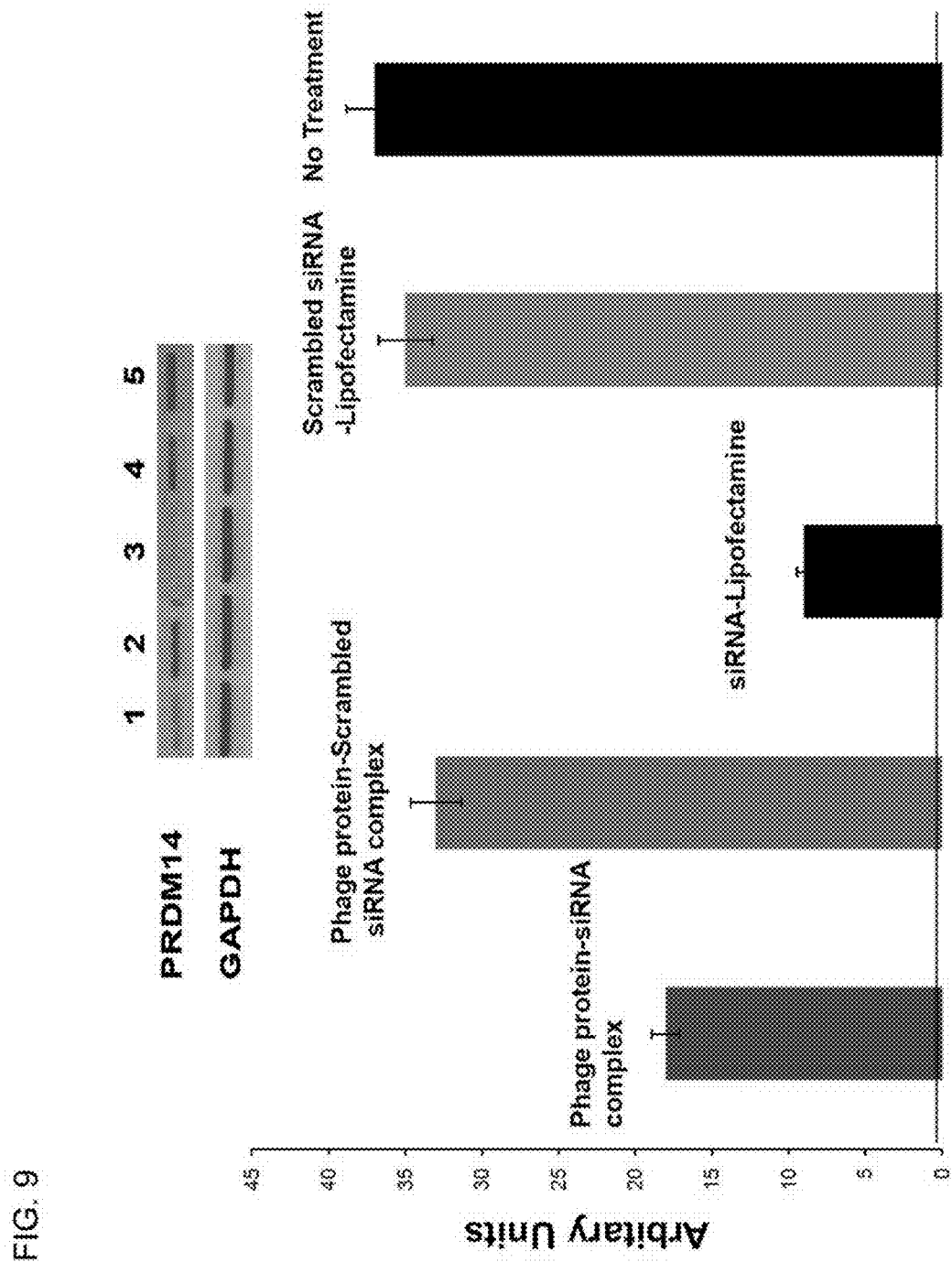
FIG. 9. illustrates RT-PCR analysis of gene transcription in MCF-7 cells treated with phage-siRNA complexes, including transcription level of the target gene in cells treated with: 1. PRDM14-targeted phage-siRNA; 2. phage-siRNA scrambled; 3. PRDM14-targeted siRNA-lipofectamine, 4. Scrambled siRNA-lipofectamine, 5. Control (no treatment).
Figure 10:
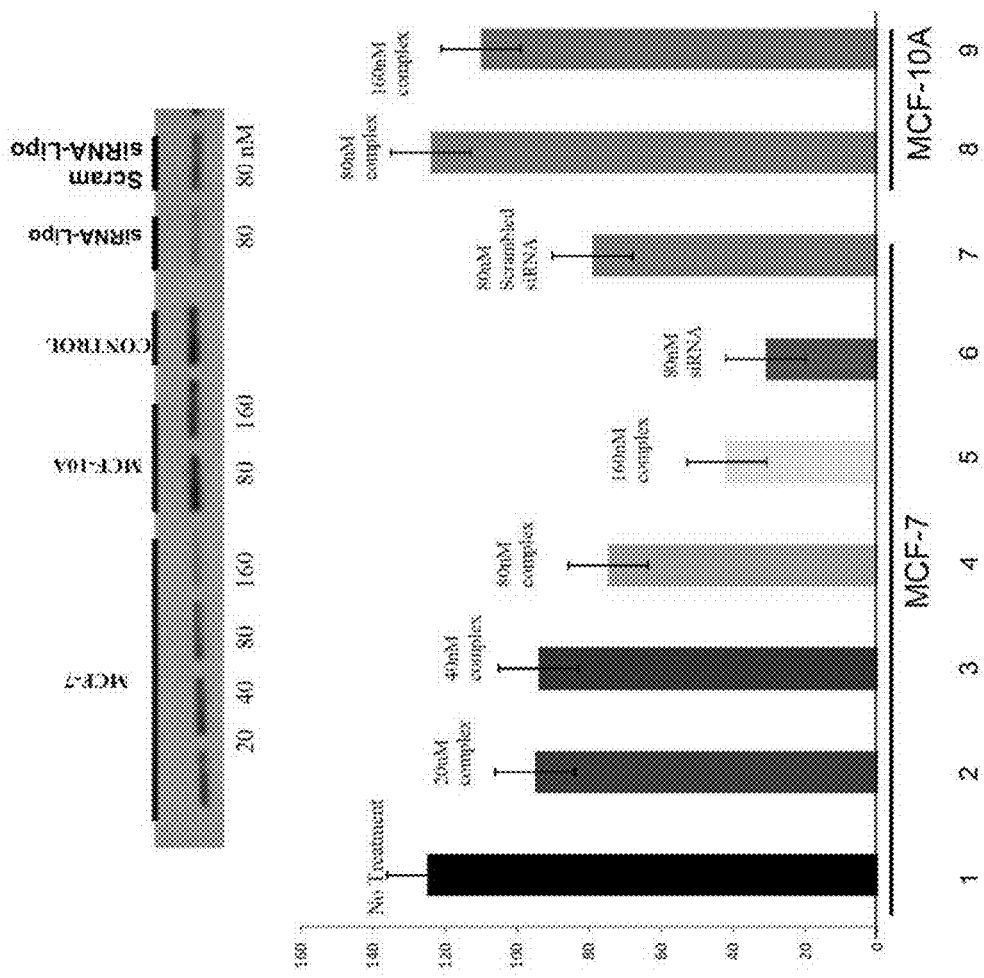
FIG. 10. A. illustration of RT-PCR analysis of relative GAPDH gene transcription levels in cells treated with VEEGGYIAA (SEQ ID NO:7) phage-siRNA complexes or siRNA-lipofectamine: No Treatment (1), 20 nM complex (2), 40 nM complex (3), 80 nM complex (4) and 160 nM complex (5), 80 nM siRNA-lipofectamine (6), 80 nM scrambled siRNA-lipofectamine. Relative transcription level of GAPDH gene transcription in MCF-10A cells treated with 80 nM complex (8); and 100 nM complex (9).

Fusion protein of phage VEEGGYIAA (SEQ ID NO:7) was isolated in octameric form by size exclusion chromatography of cholate-solubilized phage[17]. This inexpensive procedure allows obtaining 10-20 mg of a pure target-specific phage coat protein from 1 L of culture and can be optimized and scaled up. A complex of the phage protein with AlexaFluor-488-labeled siRNA (molar ratio 80:1) was obtained by gradual decrease of concentration of cholate by ultrafiltration. Encapsulation of siRNA and its release after digestion of the protein by protease K was controlled by agarose gel electrophoresis (FIG. 7). When the complex was incubated with MCF-7 cells for 24 hrs, internalization of siRNA was observed by fluorescence microscopy (FIG. 8). The silencing effect of protein-targeted siRNA was tested on MCF-7 cells using proline rich domain-14 (PRDM 14) gene as a model. Protein-targeted PRDM-14-specific siRNA down-regulated PRDM-14 gene expression by 40% as compared to targeted scrambled siRNA (FIG. 9). Gene specificity and cell targeting potential of complexes of phage proteins with siRNA was also demonstrated using another model-gene glyceraldehyde 3-phosphate dehydrogenase (GAPDH) in cancer and normal cells MCF-7 and MCF-10A (FIGS. 10 and 11).

MCF-7 cells were treated with phage-siRNAs comprising siRNA targeted to GADPH. FIG. 10 illustrates RT-PCR analysis of GAPDH gene transcription cells treated with VEEGGYIAA (SEQ ID NO:7) phage-siRNA complexes or siRNA-lipofectamine. FIG. 11 illustrates an analysis of GAPDH protein expression by Western blot. MCF-7 or MCF-100A cells were treated with VEEGGYIAA phage-siRNA complex (80/1) (50 nM siRNA) or control VEEGGYIAA phage-NesiRNA (50 nM siRNA) and incubated for 72 h. Cells were lysed and portion of cell extract was run on 4-20% Tris-HCl gel, transferred to PVDF membrane and probed with monoclonal anti-GAPDH antibody (1:2000 dilution) followed by incubation with peroxidase-conjugated Affinipure Goat Anti-mouse IgG (1:5000). The bands corresponding to GAPDH were visualized using chemiluminescent substrate solution. Membranes were treated with the Western blot stripping buffer and probed with polyclonal anti-β-Actin antibody (1:2000) followed by incubation with peroxidase-conjugated Affinipure Goat Anti-rabbit IgG (1:5000). The bands corresponding to actin were visualized using chemiluminescent substrate solution.

These data can justify the idea of using phage protein-targeted siRNA as breast cancer-specific therapeutics. The results show that siRNAs targeted to the breast cancer cells MCF-7 via their encapsulation by phage fusion proteins down-regulated targeted gene expression and inhibited protein synthesis in MCF-7 cells.

Conclusion

The landscape phage bearing MCF-7-specific peptide, VEEGGYIAA (SEQ ID NO:7) was selected from a landscape library f8/8 and a biopanning protocol against MCF-7 cells. Phage fusion protein-siRNA complex was formed by self-assembly of VEEGGYIAA (SEQ ID NO:7) phage protein and PRDM14 or GAPDH specific siRNAs. Delivery of gene specific siRNAs via the complex downregulated their corresponding gene expression in MCF-7 cells but not in MCF-10A cells, demonstrating that pVIII coat protein displaying cancer cell-targeting peptides can be effectively used to deliver siRNA into the target cells and silence target specific genes.

Example 2

Targeted Delivery of siRNA into Breast Cancer Cells Via Landscape Phage Fusion Proteins Abstract Chemotherapy plays a minimal role in recurrent settings of breast cancer where the tumor is in the chemotherapy refractory state. The resistance of breast cancer cells to cytotoxic drugs is acquired mainly due to the overproduction of some proteins, such as MDR1/Pgp, MRP1, BRCP and PARP, which protect the cells in different ways against cytotoxic anti-tumor agents, such as doxorubicin. Effectiveness of chemotherapy can be increased by supplementing chemotherapy with siRNA that inhibits the synthesis of drug-resistance proteins. Although unprotected "naked" siRNAs have demonstrated significant specific effect in some model systems, a systemic use of naked siRNA medicines is hindered by their fast destruction in physiological liquids, insufficient tissue bioavailability and poor cellular uptake. A challenge for clinical use of siRNAs as anti-breast cancer drugs is development of tumor selective, stable, active and physiologically stable targeting carriers that would make stable complexes with siRNA, protect them from degradation, deliver them to the tumors and control their unloading inside the cancer cells. Disclosed here are phage-fusion protein-siRNA-nanoparticles, "phage-siRNAs", in which siRNAs are encapsulated and targeted to breast tumors by phage fusion proteins with high selectivity, affinity and stability. It is hypothesized that silencing of genes that relate to tumor drug resistance by targeting of siRNAs via breast cancer specific phage proteins may significantly enhance the sensitivity of tumor cells to chemotherapy.

Introduction

Breast cancer is the most common cancer and the second leading cause of cancer death in American women. Despite advances in early detection and understanding of breast cancer mechanisms, about 30% of cured patients with early-stage breast cancer have recurrent disease. Their treatment may require systemic chemotherapy using cytotoxic, hormonal, and immunotherapeutic agents. In general, systemic agents are effective at the beginning of therapy in 90% of primary breast cancers and 50% of metastases[1]. However, after a certain period, progression occurs. At that point, tumor cells become resistant to systematic therapy. It was shown that resistance of breast cancer cells to chemotherapy can be eliminated or essentially decreased by the use of small (short) interfering RNAs (siRNAs) that inhibit synthesis of proteins related to tumor drug resistance[2]. However, a systematic use of siRNAs is hindered by their instability in physiological liquids, limited tissue bioavailability and poor cellular uptake. Cellular delivery and bioavailability of siRNA can be increased by their encapsulation into nanoparticulate carriers[3], or association with cell penetrating peptides (CPP)[4,5,6]. Efficacy of siRNA nanomedicines can be further enhanced by their conjugation with cell-targeting ligands (CTL) that bind to cancer-specific cellular receptors[7,8]. The availability of combinatorial peptide libraries adds another availing dimension to the concept of the targeted antitumor pharmaceuticals[8,9]. They provide a rich source of peptides targeted to specific tissue, cell, receptor or cellular compartments.

Figure 5:
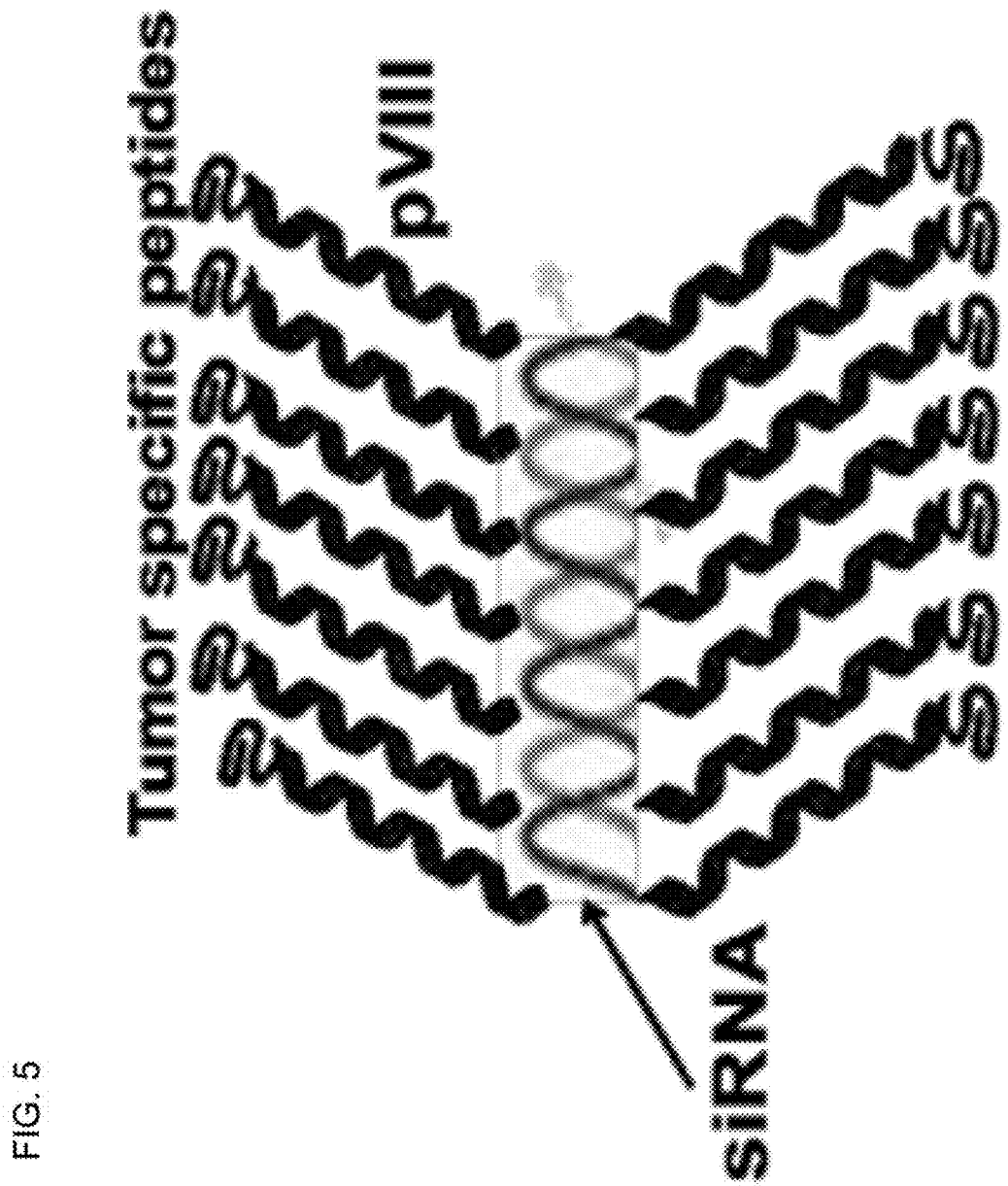
FIG. 5. illustrates tumor-targeted phage-like nanoparticles with entrapped siRNA. siRNA is depicted as a double helix. Fusion pVIII proteins are depicted as alpha-helixes with disordered fused tumor-specific peptides.

A new challenge, within the frame of the emerging concept of targeted siRNA delivery is development of highly selective, stable, active and physiologically acceptable ligands that would protect siRNAs against degradation in the blood stream, navigate them to the site of disease and provide a means for their penetration into the target cancer cells. To respond to this challenge, siRNA-nanoparticles are proposed, in which siRNA is encapsulated and targeted to the breast tumor cells by phage fusion proteins having high selectivity, affinity and stability. The tumor-specific fusion phage proteins can be isolated from phage particles affinity selected from multibillion clone libraries by their ability to bind cancer cells very specifically and penetrate into the cells or accumulate in the tumor-surrounding vasculature. Phage proteins can be converted then into siRNA-phage protein complexes, named "phage-siRNAs", by their self-assembly, as illustrated in FIGS. 3-5. Gene silencing siRNA may be encapsulated and protected in the phage-siRNA particle and can be targeted to cells, tissues and organs via a binding peptide on the phage (e.g., presented by the pVIII major coat protein) for selective delivery of gene silencing siRNA.

Phage display technology is based on a genetic fusion of phage coat proteins with foreign peptides to achieve their surface display on a viable and infective virion[16]. Foreign peptides have been displayed on the pVIII protein and the pIII minor coat protein[9,10]. In the pVIII display format (landscape phage), the guest peptide is fused to every pVIII subunit, increasing the virion's mass by up to 20%. Such particles retain their ability to infect host *E. coli* bacteria and form phage progeny. Landscape phage and their isolated fusion proteins have been shown to serve as substitutes for antibodies against various antigens and receptors, including cancer cells, in drug/gene-delivery vehicles and biosensors[11,16]. Recent studies have shown that landscape phage proteins can serve as ligands that target doxorubicin-containing liposomes (Doxil) to cancer cells and enhance their cytotoxic effects[12,19].

Landscape phage represents an attractive platform for targeted siRNA delivery due to its unique characteristics: a) the phage capsid formed by ~4,000 domains of the coat protein associated with phage DNA is very stable and is resistant to stressful aggressive media and high temperature[13,14]; b) reproduction of phage relies on powerful and natural mechanisms of phage infection, biosynthesis and self-assembly; and c) tumor-targeted landscape phages can be affinity selected from multibillion clone libraries due to their ability to bind very specifically to cancer cells, penetrate into the cells or accumulate in the tumor-surrounding vasculature. Importantly, selection of phage that binds or internalizes into cancer cells can be designed, so that only phage capable of internalizing and escaping endosomes are selected[20], where endosomal escape of siRNA from the vehicle carrying the siRNA is desirable for biological activity of the siRNA; d) targeted fusion phages are able to penetrate into mammalian cells, survive inside cellular compartments and deliver gene into target cells[15,16]. In view of these properties of phage as an efficient natural delivery system, the phage-like platform may provide a superior vehicle for siRNA delivery, for example to cancer cells such as breast cancer cells. The proposed new strategy of siRNA delivery to breast cancer cells explores the unique propensity of phage proteins to self-assemble in the presence of nucleic acids and to form particles mimicking the structure of the phage capsid[15,16]. Owing to high stability of assembled phage proteins in stressful environments and their tight association with nucleic acid, siRNA may be shielded and protected from serum endonucleases and other distressing environmental factors. At the same time, phage capsid becomes unstable when phage interacts with cellular membranes which may enable a release of encapsulated siRNA inside the cells. Furthermore, phage fusion protein can target siRNA specifically not only to a target cell but can navigate it further to a specific cytoplasmic destination. Therefore, phage-siRNAs may provide a highly selective, stable, active and physiologically acceptable breast cancer nanomedicine.

Furthermore, complexes of siRNAs with breast cancer-specific phage fusion proteins may significantly enhance the sensitivity of tumor cells to chemotherapy where the siRNA silences genes related to tumor drug resistance. For example, silencing of breast cancer-specific genes in patients may be achieved by administering to the patients preparations of siRNAs self-assembled with phage proteins that are targeted to breast cancer cells. The phage proteins may protect siRNAs against degradation and mediate their efficient internalization into the breast cancer cells, thereby inducing siRNA-specific gene silencing. The proposed technique may be tested and optimized using model doxorubicin-resistant breast cancer cells MDA-MB-231 and representative gene PARP-1 encoding poly(ADP-ribose) polymerase-1. Doxorubicin induces expression of the PARP-1 gene which subsequently causes resistance of the cells to treatment with doxorubicin. Inhibition of PARP-1 gene expression potentiates the effect of doxorubicin[18] suggesting that PARP-1 gene expression has an active role in development of chemoresistant status in breast cancer cells. The MDA-MB-231/PARP-1 model may demonstrate specificity and selectivity of targeted nanomedicines both in vitro which subsequently may be confirmed in vivo using a mice xenograft models.

Accordingly, landscape phage libraries f8/8 and f8/9[10,21] may be used to select phage binding to MDA-MB-231 cells. Four rounds of selection may be performed and the isolated clones may be identified by their DNA sequence. Binding specificity of the phage may be determined in a phage capture assay[12]. Phage fusion proteins may be isolated by stripping the phage and may be purified from viral DNA and traces of other proteins by size-exclusion chromatography. PARP-1-targeted siRNAs or scrambled siRNAs may be mixed with increasing concentrations of phage proteins, to provide phage protein/siRNA complexes. Complexes with optimized compositions of siRNAs and proteins may be purified by size-exclusion chromatography and analyzed by electrophoresis. Size distribution of the phage protein/siRNA complexes may be analyzed by dynamic light scattering. Efficacy of intracellular delivery of fluorescent siRNA may be determined using microscopy.

The cytotoxic potential of doxorubicin and Doxil may be studied in combination with phage-siRNAs (targeted to PARP-1) and control complexes, as described below. Activation of gene PARP-1 by doxorubicin and effect of the phage-siRNAs on PARP-1 mRNA and protein levels may be determined by RT-PCR and western blot analysis. Stability, uptake, and antitumor effect of phage-siRNA complexes in comparison with control preparations may be tested in mice with xenografts of MDA-MB-231 cells, as described in detail below.

Methods

Phage Libraries and Selection Procedures.

Cancer cell-binding phages may be obtained using established selection protocols[14]. An aliquot of the library (~$10^{11}$ virions) in a washing/blocking buffer may be added to an empty depletion flask and incubated for 1 h at 20° C. Non-bound phages may be transferred to another depletion flask treated with serum, and then to a depletion flask containing non-target cells MCF-10A. Cell surface-bound phage may be retrieved with acid elution buffer. The eluate may be neutralized and concentrated by ultrafiltration. To recover cell-penetrating phage, cells may be scraped, pelleted by centrifugation and lysed in 2% sodium deoxycholate buffer. Both phage fractions (eluted fraction and lysis fraction) may be amplified separately and used in subsequent rounds of selection. Phage input/output ratio may be followed by phage titering. Following the 4-6th round, a segment of phage gene VIII DNA from 100 individual clones may be amplified by PCR and sequenced to reveal the protein sequences responsible for binding to the cells.

Binding specificity and selectivity of phages may be determined in a phage capture assay adapted for 96-well culture plate format[12]. Selectivity of phages may be determined by measuring their binding to target cancer cells in comparison with serum, control normal and other cancer cells. Briefly, amplified test phages and control phages may be incubated with MDA-MB-231 target cells, control epithelial MCF-10A cells, unrelated hepatocellular carcinoma HepG2 cancer cells and control serum-treated wells. Unbound phages may be washed away and bound phages may be recovered with CHAPS buffer. The amount of phage in fractions may be determined by its titering in *E. coli* K91 BlueKan host bacterial cells. Phage recovery may be expressed as a ratio of input to output phage. To determine a localization of phages in the cells, cell-associated phages may be eluted with acid buffer. Next, the cells may be washed with neutral buffer and finally with CHAPS buffer for recovery of cell-penetrated phage particles, To determine a role of cell metabolism in association of the phage with live cells, the incubation of phage with cells may be carried out at 20° C. and at 37° C. with and without serum.

Fusion Phage Proteins.

Phage fusion 55- or 56-mer coat proteins with general formula AXXXXXXXXDPAKAAFDSLQASATEYI-GYAWAMVVVIVGATIGIKLFKKFTSKAS (SEQ ID NO:3), where X is a random amino acid or AXXXXXXXXX-PAKAAFDSLQASATEYIGYAWAMVVVIV-GATIGIKLFKKFTSKAS (SEQ ID NO:4), may be prepared by stripping phage virions in cholate[22]. Briefly, the mixture (1:2 v/v) of phage in TBS buffer (~1 mg/ml), 120 mM cholate in 10 mM Tris-HCl, 0.2 mM EDTA, pH 8.0, and 5% chloroform may be incubated overnight at 37° C. on rotator. The protein may be purified by size-exclusion chromatography using a Sepharose 6B-CL column (1 cm×45 cm), eluted with 100 mM cholate in 10 mM Tris-HCl, 0.2 mM EDTA pH 8.0. The chromatographic profile may be controlled by Econo UV monitor. The isolated protein typically is an aggregate with molecular weight ~46 KDa (8-mer) determined by chromatography on a calibrated column. Concentration of proteins may be measured spectrophotometrically using their molar extinction calculated using PROTEAN program (DNA STAR Inc., Madison, Wis.).

Preparation and Characterization of Targeted Phage-siRNA Preparations.

PARP-1-targeted siRNAs (sense 5'-GGAUGAUCUUC-GACGUGGA-3' (SEQ ID NO:5), antisense 5'-UCCA-CGUCGAAGAUCAUCC-3' (SEQ ID NO:6)) or scrambled siRNAs (200 nM; Invitrogen, Carlsbad, Calif.) may be mixed with 10-80-fold molar excess of phage proteins and centrifuged in 30 Kda Amicon unit and washed two times with 10 mM TrisHCl buffer to remove the detergent and form a complex comprising phage proteins and siRNA. The complex may be analyzed by: (1) agarose gel analysis with SIBR-green staining; and (2) size-exclusion chromatography. Size distribution will analyzed by the dynamic light scattering using a Beckman Coulter N4 Plus Particle analyzer (Beckman Coulter, Inc., Fullerton, Calif.).

Analysis of PARP-1 Gene Activation in MDA-MB-231 Cells.

MDA-MB-231 cells grown during 24 h in a 6-well plate/well may be treated with Doxil (10-200 µg/ml) for 1 hr. Total RNA may be extracted using Micro RNA isolation kit (Qiagen, GmbH, Hilden, Germany) and RT-PCR may be performed to determine the level of PARP-1 gene expression. To determine a level of PARP-1 protein synthesis, cells may be lysed with 70 µL of RIPA buffer (Sigma) containing protease inhibitor cocktail (7 µL) and 2 mM PMSF. The protein concentration in whole cell lysate may be measured by Biorad DC protein assay. Cell extract may be separated by gel-electrophoresis (4-20%; Biorad) and transferred to PVDF membrane. The membrane may be blocked in wash buffer (PBS, 5% nonfat dry milk) at 20° C. for 1 h; incubated overnight at 4° C. with polyclonal anti-PAR-1 antibody (1:500 dilution) (Trivegen); washed with PBS/0.5% Tween-20 four times; incubated with peroxidase-conjugated Affinipure Goat Anti-rabbit IgG (1:5000) (Jackson Immunoresearch) at 20° C. for 1 h; washed with PBS/0.5% Tween-20 four times; incubated with 5 ml of West Pico Luminol/Enhancer Solution and 5 ml West Pico Stable Peroxide Solution (Pierce Super Signal West Pico Biotin detection Kit) for 10 min; stripped using the western blot stripping buffer for 10 min; probed with monoclonal anti-PARP-1 antibody (1:2000) for 1 hr; loaded on to a cassette and exposed to radiographic film for 1-2 min. Images may be scanned using a scanner and quantified by NIH image J software.

Knockdown of Target Gene.

MDA-MB-231 cells grown in a 6-well plate may be treated with Doxil (10-200 g/ml) for 1 hr. Media may be replaced with fresh media containing complexes of a) phage proteins with siRNAs targeted to PARP-1; b) phage protein with scrambled siRNA, c) non-related phage protein with siRNA targeted to PARP-1; or d) complex of lipofectamine with siRNA targeted to PARP-1. Plates may be incubated for 24 hr in DMEM supplemented with 10% FBS at 37° C. in a humidified 5% $CO_2$ incubator. Total RNA may be extracted at 24-72 h time points using Micro RNA isolation kit (Qiagen, GmbH, Hilden, Germany), and the knockdown of PARP-1 gene by phage protein-siRNA or siRNA-lipofectamine preparations may be determined by RT-PCR using One step Access RT-PCR kit (Promega). A level of PARP-1 protein synthesis will be analyzed by western blot as describe above.

Cytotoxicity Assay.

Cells may be grown in 96-well plates to ~75% confluence to obtain ~$5 \times 10^5$ cells/well. The plates may be washed twice with serum-free DMEM media and treated with Doxil (10-200 µg/ml) for 1 hr. After 1 hr, media may be replaced and fresh media containing complexes of a) phage proteins with siRNA targeted to PARP-1, b) phage protein with scrambled siRNA, non-related phage-protein with siRNA targeted to PARP-1, or c) lipofectamine with siRNA targeted to PARP-1. After incubation for 24-72 h in DMEM supplemented with 10% FBS at 37° C. in a humidified 5% $CO_2$ incubator, the plates may be washed 3 times with serum-free DMEM media, and incubated with CellTiter 96® Aqueous One solution for 1-4 hrs at 37° C., 5% $CO_2$. The cell survival rate may be estimated by measuring the absorbance of the MTS degradation product at 492 nm using the Tecan SpectraFluor Plus plate reader (Tecan Systems, Inc., San Jose, Calif.).

Tumor Inoculation in Mice.

The experiments may be performed in BALB/c/nu/nu (nude) mice (n=15; Charles River Laboratories, Wilmington, Mass.). The protocol may be approved by Institutional animal care and use committee (I-COOK committee) of Auburn University and Northeastern University. MDA-MB-231 cells may be grown in the logarithmic phase, centrifuged (100 r/min, 5 min) and the supernatant removed. Each nude mouse may be injected with 0.2 ml (i.e., $5 \times 10^6$ cells) cell suspension in the subcutaneous layer in the right lower back using a 1-ml syringe. Tumors may be grown while keeping animals in aseptic conditions for 7-10 days until the tumor can be discovered by direct palpation. There may be at least 5 animals in each group. Experimental mice bearing a tumor xenograft may be treated at chosen times with Doxil and protein/siRNA formulations intravenously. Complex formulations and controls may be given twice per week for a total of 5 weeks. The mice may be monitored daily for tumor size. Tumor measurements may be performed using calipers to measure the tumor in two dimensions, at the longest and widest points at approximately 90° C. to each other. Tumor volume may be calculated as: Volume=(width$^2$×length)/2. Antitumor activity may be assessed according to the guidelines established by the National Cancer Institute. Microscopic postmortem tumor tissue examination may be performed using a standard hematoxylyn/eosin staining.

Accumulation of Phage-siRNAs in Tumors.

The experiments may be performed in nude mice following the above-described protocol, which may be approved by the Institutional Animal Care and Use Committee. The mice may be injected with targeted phage-siRNAs in the tail vein (approx. 10 days after tumor inoculation). At 1, 3, 6, and 24 h post injection, mice may be sacrificed by $CO_2$ euthanasia. Tumors may be removed, imbedded in paraffin and sectioned. Tumor sections may be incubated with anti-fd phage antibody (1:500) and visualized under microscope.

Assessment of Therapeutic Anticancer Effect of Phase-siRNAs.

Mice inoculated with MDA-MB-231 tumor cells (5 mice per group) may be treated twice weekly with a) Doxil, b) Doxil and phage-siRNAs (targeted to PARP-1) preparation, c) Doxil and phage-siRNAs (scrambled), d) Doxil and non-related phage-siRNA (targeted to PARP-1), or e) siRNA alone for 7 weeks through intravenous injection. The dosing regimen may be adjusted based on the analysis of the intratumoral drug accumulation, as described. The mice may be monitored on alternate days for tumor size for 5 weeks depending on the tumor type and examined routinely for tumor appearance. Tumor measurements may be performed as described above. Microscopic postmortem tumor tissue examination may be performed using a standard hematoxylyn/eosin staining, apoptotic staining using TUNEL kit (ApoAlert, BD Biosciences) and immunohistochemistry using phospho-Ser473 Akt antibody (Cell Signaling) with VectaStain IHC peroxidase kit (Vector Labs). Angiogenesis in the tumors may be assessed by assessment of microvessel density following staining of the tumor sections with anti-CD31 antibody (Santa Cruz).

Statistical Treatment of the Data to be Obtained.

The choice of statistical tests, as well as of group size for both in vitro and in vivo experiments may be made according to the principles formulated by Siegel[23]. Each in vitro experiment will include 4-5 points for each measurement, and each animal experiment will include 5-6 mice and may be repeated twice. In vitro data may be analyzed using the Student's t-test for two independent samples and two-way ANOVA analysis with Tukey's HSD Post-Hoc test for three or more independent samples. These tests may be analyzed using Kaliedagraph® software, version 3.6 (Synergy Software, Reading, Pa.). Non-parametric, Wilcoxon rank sum test may be used to evaluate the results on the tumor accumulation and inhibition for various formulations. The exact probability values under the randomization test may be computed with the aid of the software RS1. $P<0.05$ may be considered significant. If required, the survival data may be analyzed by log rank Kaplan-Meier method using GraphPad P.

REFERENCES

1. Gonzalez-Angulo, A. M., Morales-Vasquez, F., & Hortobagyi, G. N. Overview of resistance to systemic therapy in patients with breast cancer. *Adv. Exp. Med. Biol.* 608, 1-22 (2007).
2. Wu, H., Hail, W. N., & Yang, J. M. Small Interfering RNA-induced Suppression of MDRI (P-Glycoprotein) Restores Sensitivity to Multidrug-resistant Cancer Cells. *Cancer Res* 63, 1515-1519 (2003).
3. Foged, C., Nielsen, H. M., & Frokjaer, S. Liposomes for phospholipase A2 triggered siRNA release: Preparation and in vitro test. *International Journal of Pharmaceutics* 331, 160-166 (2007).
4. Crombez, L, Charnet, A., Morris, M. C., drian-Herrada, G., Heitz, F., & Divita, G. A non-covalent peptide-based strategy for siRNA delivery. *Biochem. Soc. Trans.* 35, 44-46 (2007).
5. Striab-Fisher, A., Sergueev, D. S., Fisher, M., Shaw, B. R., & Juliano, R L. Antisense inhibition of P-glycoprotein expression using peptide-oligonucleotide conjugates. *Biochem. Pharmacol.* 60, 83-90 (2000).
6. Crombez, L, Morris, M. C., Dufort, S., drian-Hermda, G., Nguyen, Q., McMaster, G., Coll, J. L., Heitz, F., & Divita, G. Targeting cyclin B1 through peptide-based delivery of siRNA prevents tumour growth. *Nucl. Acids Res.* 37, 4559-4569 (2009).
7. Tian, X., Aruva, M. R., Qin, W., Zhu, W., Sauter, E. R, Thakur, M. L., & Wickstrom, E. Noninvasive molecular imaging of MYC mRNA expression in human breast cancer xenografts with a [99 mTc]peptide-peptide nucleic acid-peptide chimera 7. *Bioconjug. Chem.* 16, 70-79 (2005).
8. Cesarone, G., Garofalo, C., Abrams, M. T., Igoueheva, O., Alexeev, V., Yoon, K., Surrnacz, E., & Wickstrom, E. RNAi-mediated silencing of insulin receptor substrate I (IRS-I) enhances tamoxifen-induced cell death in MCF-7 breast cancer cells 4. *J Cell Biochem.* 98, 440-450 (2006).
9. Krumpe, L. R. & Mori, T. Potential of phage-displayed peptide library technology to identify functional targeting peptides. *Expert Opinion on Drug Discovery* 2, 525-537 (2007).)
10. Petrenko, V. A., Smith, G. P., Gong, X., & Quinn, T. A library of organic landscapes on filamentous phage 29. *Protein Eng* 9, 797-801 (1996).
11. Lakshmanan, R S., Guntupalli, R., Hu, J., Kim, D. J, Petrenko, V. A., Barbaree, J. M., & Chin, B. A. Phage immobilized magnetoelastic sensor for the detection of *Salmonella typhimurium*. *J. Microbial. Methods* 71, 55-60 (2007).
12. Jayanna, P. K., Bedi, D., Gillespie, J. W., Deinnocentes, P., Wang, I., Torchilin, V. P., Bird, R. C., & Petrenko, V. A. Landscape phage fusion protein-mediated targeting of nanomedicincs enhances their prostate tumor cell association and cytotoxic efficiency. *Nanomedicine*. (20 I0).
13. Olofsson, L., Ankarloo, J., & Nicholls, I. A. Phage viability in organic media: insights into phage stability. *J. Mol. Recognit.* 11, 91-93 (1998).
14. Brigati, J. R., Samoylova, T. I., Jayannu, P. K., & Petrenko, V. A. Phage display for generating peptide reagents. *Curr. Protoc. Protein Sci. Chapter* 18, Unit (2008).
15. Mount, J. D., Samoylova, T. I., Morrisoll, N. E., Cox, N. R., Baker, H. J., & Petrenko, V. A. Cell targeted phagemid rescued by preselected landscape phage. *Gene* 341, 59-65 (2004).

16. Petrenko, V. Evolution of phage display: from bioactive peptides to bioselective nanomaterials. *Expert. Opin. Drug Deliv.* 5, 825-836 (2008).
17. Jayanna, P. K., Bedi, D., Deinnocentes, P., Bird, R. C., & Petrenko, V. A. Landscape phage ligands for PC3 prostate carcinoma cells. *Protein Eng Des Sel*. (2010).
18. Munoz-Gamez, J. A., Martin-Oliva, D., guilar-Quesada, R., Canuelo, A., Nunez, M. I., Valenzuela, M. T., Ruiz de Almodovar, J. M., de, M. G., & Oliver, F. J. PARP inhibition sensitizes p53-deficicnl breast cancer cells to doxorubicin-induced apoptosis. *Biochem. J.* 386, 119-125 (2005).
19. Tao Wang, Gerard G. M. D'Souza, Deepa Bedi, Olusegtul A. Fagbohun, L. Prasanna Potturi, Brigitte Papahadjopoulos-Sternberg, Valery A Petrenko, and Vladimir P Torchilin. Tumor-Specific Phage Fusion Coat Protein-Modified Drug-Loaded Liposomes Show Enhanced Binding 3nd Killing of Target Tumor Cells Proc. *Future Medicine: Nanomedicine* (2009). (In Press).
20. Tao Wang, Shenghong Yang, Valery A Petrenko, Vladimir P. Torchilin. Cytoplasmic Delivery of Liposomes into MCF-7 Breast Cancer Cells Mediated by Cell-Specific Phage Fusion Coat Protein. *Molecular Therapeutics* (2010) (Submitted).
21. Kuzmicheva, G. A., Jayanna, P. I<., Sorokulova, I. B. & Petrenko, V. A. Diversity and censoring of landscape phage libraries. *Protein Eng Des Sel* 22, 9-18 (2009).
22. Jayanna P. K., Torchilin V. P, and V. A. Petrenko (2009) Liposomes targeted by fusion phage proteins. *Nanomedicine* 1, 83-9 (2009).
23. Scheffe H. *The analysis of variance*. New York: Wiley; 1959.
24. Smith G. P. and Petrenko V. A. Phage Display. *Chemical Reviews*, 97, 391-410 (1997).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

TABLE 1

| | |
|---|---|
| ABL1 | v-abl Abelson murine leukemia viral oncogene homolog 1 |
| ABL2 | v-abl Abelson murine leukemia viral oncogene homolog 2 |
| ACSL3 | acyl-CoA synthetase long-chain family member 3 |
| AF15Q14 | AF15q14 protein |
| AF1Q | ALL1-fused gene from chromosome 1q |
| AF3p21 | SH3 protein interacting with Nck, 90 kDa (ALL1 fused gene from 3p21) |
| AF5q31 | ALL1 fused gene from 5q31 |
| AKAP9 | A kinase (PRKA) anchor protein (yotiao) 9 |
| AKT1 | v-akt murine thymoma viral oncogene homolog 1 |
| AKT2 | v-akt murine thymoma viral oncogene homolog 2 |
| ALDH2 | aldehyde dehydrogenase 2 family (mitochondrial) |
| ALK | anaplastic lymphoma kinase (Ki-1) |
| ALO17 | KIAA1618 protein |
| APC | adenomatous polyposis of the colon gene |
| ARHGEF12 | RHO guanine nucleotide exchange factor (GEF) 12 (LARG) |
| ARHH | RAS homolog gene family, member H (TTF) |
| ARID1A | AT rich interactive domain 1A (SWI-like) |
| ARNT | aryl hydrocarbon receptor nuclear translocator |
| ASPSCR1 | alveolar soft part sarcoma chromosome region, candidate 1 |
| ASXL1 | additional sex combs like 1 |
| ATF1 | activating transcription factor 1 |
| ATIC | 5-aminoimidazole-4-carboxamide ribonucleotide formyltransferase/IMP cyclohydrolase |
| ATM | ataxia telangiectasia mutated |
| ATRX | alpha thalassemia/mental retardation syndrome X-linked |
| BAP1 | BRCA1 associated protein-1 (ubiquitin carboxy-terminal hydrolase) |
| BCL10 | B-cell CLL/lymphoma 10 |
| BCL11A | B-cell CLL/lymphoma 11A |
| BCL11B | B-cell CLL/lymphoma 11B (CTIP2) |
| BCL2 | B-cell CLL/lymphoma 2 |
| BCL3 | B-cell CLL/lymphoma 3 |
| BCL5 | B-cell CLL/lymphoma 5 |
| BCL6 | B-cell CLL/lymphoma 6 |
| BCL7A | B-cell CLL/lymphoma 7A |
| BCL9 | B-cell CLL/lymphoma 9 |
| BCR | breakpoint cluster region |
| BHD | folliculin, Birt-Hogg-Dube syndrome |
| BIRC3 | baculoviral IAP repeat-containing 3 |
| BLM | Bloom Syndrome |
| BMPR1A | bone morphogenetic protein receptor, type IA |
| BRAF | v-raf murine sarcoma viral oncogene homolog B1 |
| BRCA1 | familial breast/ovarian cancer gene 1 |
| BRCA2 | familial breast/ovarian cancer gene 2 |
| BRCP | breast cancer resistance protein |
| BRD3 | bromodomain containing 3 |
| BRD4 | bromodomain containing 4 |
| BRIP1 | BRCA1 interacting protein C-terminal helicase 1 |
| BTG1 | B-cell translocation gene 1, anti-proliferative |
| BUB1B | BUB1 budding uninhibited by benzimidazoles 1 homolog beta (yeast) |
| C12orf9 | chromosome 12 open reading frame 9 |
| C15orf21 | chromosome 15 open reading frame 21 |
| C15orf55 | chromosome 15 open reading frame 55 |
| C16orf75 | chromosome 16 open reading frame 75 |
| CANT1 | calcium activated nucleotidase 1 |
| CARD11 | caspase recruitment domain family, member 11 |
| CARS | cysteinyl-tRNA synthetase |
| CBFA2T1 | core-binding factor, runt domain, alpha subunit 2; translocated to, 1 (ETO) |
| CBFA2T3 | core-binding factor, runt domain, alpha subunit 2; translocated to, 3 (MTG-16) |
| CBFB | core-binding factor, beta subunit |
| CBL | Cas-Br-M (murine) ecotropic retroviral transforming |
| CBLB | Cas-Br-M (murine) ecotropic retroviral transforming sequence b |
| CBLC | Cas-Br-M (murine) ecotropic retroviral transforming sequence c |
| CCNB1IP1 | cyclin B1 interacting protein 1, E3 ubiquitin protein ligase |
| CCND1 | cyclin D1 |
| CCND2 | cyclin D2 |
| CCND3 | cyclin D3 |
| CD273 | programmed cell death 1 ligand 2 |
| CD274 | CD274 molecule |
| CD74 | CD74 molecule, major histocompatibility complex, class II invariant chain |
| CD79A | CD79a molecule, immunoglobulin-associated alpha |
| CD79B | CD79b molecule, immunoglobulin-associated beta |
| CDH1 | cadherin 1, type 1, E-cadherin (epithelial) (ECAD) |
| CDH11 | cadherin 11, type 2, OB-cadherin (osteoblast) |
| CDK4 | cyclin-dependent kinase 4 |

TABLE 1-continued

| | |
|---|---|
| CDK6 | cyclin-dependent kinase 6 |
| CDKN2A - p16(INK4a) | cyclin-dependent kinase inhibitor 2A (p16(INK4a)) gene |
| CDKN2A- p14ARF | cyclin-dependent kinase inhibitor 2A- p14ARF protein |
| CDKN2C | cyclin-dependent kinase inhibitor 2C (p18, inhibits CDK4) |
| CDX2 | caudal type homeo box transcription factor 2 |
| CEBPA | CCAAT/enhancer binding protein (C/EBP), alpha |
| CEP1 | centrosomal protein 1 |
| CHCHD7 | coiled-coil-helix-coiled-coil-helix domain containing 7 |
| CHEK2 | CHK2 checkpoint homolog (*S. pombe*) |
| CHIC2 | cysteine-rich hydrophobic domain 2 |
| CHN1 | chimerin (chimaerin) 1 |
| CIC | capicua homolog (*Drosophila*) |
| CIITA | class II, major histocompatibility complex, transactivator |
| CLTC | clathrin, heavy polypeptide (Hc) |
| CLTCL1 | clathrin, heavy polypeptide-like 1 |
| CMKOR1 | chemokine orphan receptor 1 |
| COL1A1 | collagen, type I, alpha 1 |
| COPEB | core promoter element binding protein (KLF6) |
| COX6C | cytochrome c oxidase subunit VIc |
| CREB1 | cAMP responsive element binding protein 1 |
| CREB3L1 | cAMP responsive element binding protein 3-like 1 |
| CREB3L2 | cAMP responsive element binding protein 3-like 2 |
| CREBBP | CREB binding protein (CBP) |
| CRLF2 | cytokine receptor-like factor 2 |
| CRTC3 | CREB regulated transcription coactivator 3 |
| CTNNB1 | catenin (cadherin-associated protein), beta 1 |
| CYLD | familial cylindromatosis gene |
| D10S170 | DNA segment on chromosome 10 (unique) 170, H4 gene (PTC1) |
| DAXX | death-domain associated protein |
| DDB2 | damage-specific DNA binding protein 2 |
| DDIT3 | DNA-damage-inducible transcript 3 |
| DDX10 | DEAD (Asp-Glu-Ala-Asp) box polypeptide 10 |
| DDX5 | DEAD (Asp-Glu-Ala-Asp) box polypeptide 5 |
| DDX6 | DEAD (Asp-Glu-Ala-Asp) box polypeptide 6 |
| DEK | DEK oncogene (DNA binding) |
| DICER1 | dicer 1, ribonuclease type III |
| DNMT3A | DNA (cytosine-5-)-methyltransferase 3 alpha |
| DUX4 | double homeobox, 4 |
| EBF1 | early B-cell factor 1 |
| EGFR | epidermal growth factor receptor (erythroblastic leukemia viral (v-erb-b) oncogene homolog, avian) |
| EIF4A2 | eukaryotic translation initiation factor 4A, isoform 2 |
| ELF4 | E74-like factor 4 (ets domain transcription factor) |
| ELK4 | ELK4, ETS-domain protein (SRF accessory protein 1) |
| ELKS | ELKS protein |
| ELL | ELL gene (11-19 lysine-rich leukemia gene) |
| ELN | elastin |
| EML4 | echinoderm microtubule associated protein like 4 |
| EP300 | 300 kd E1A-Binding protein gene |
| EPS15 | epidermal growth factor receptor pathway substrate 15 (AF1p) |
| ERBB2 | v-erb-b2 erythroblastic leukemia viral oncogene homolog 2, neuro/glioblastoma derived oncogene homolog (avian) |
| ERCC2 | excision repair cross-complementing rodent repair deficiency, complementation group 2 (xeroderma pigmentosum D) |
| ERCC3 | excision repair cross-complementing rodent repair deficiency, complementation group 3 (xeroderma pigmentosum group B complementing) |
| ERCC4 | excision repair cross-complementing rodent repair deficiency, complementation group 4 |
| ERCC5 | excision repair cross-complementing rodent repair deficiency, complementation group 5 (xeroderma pigmentosum, complementation group G (Cockayne syndrome)) |
| ERG | v-ets erythroblastosis virus E26 oncogene like (avian) |
| ETV1 | ets variant gene 1 |
| ETV4 | ets variant gene 4 (E1A enhancer binding protein, E1AF) |
| ETV5 | ets variant gene 5 |
| ETV6 | ets variant gene 6 (TEL oncogene) |
| EVI1 | ecotropic viral integration site 1 |
| EWSR1 | Ewing sarcoma breakpoint region 1 (EWS) |
| EXT1 | multiple exostoses type 1 gene |
| EXT2 | multiple exostoses type 2 gene |
| EZH2 | enhancer of zeste homolog 2 |
| FACL6 | fatty-acid-coenzyme A ligase, long-chain 6 |
| FANCA | Fanconi anemia, complementation group A |
| FANCC | Fanconi anemia, complementation group C |
| FANCD2 | Fanconi anemia, complementation group D2 |
| FANCE | Fanconi anemia, complementation group E |
| FANCF | Fanconi anemia, complementation group F |
| FANCG | Fanconi anemia, complementation group G |
| FBXW7 | F-box and WD-40 domain protein 7 (archipelago homolog, *Drosophila*) |
| FCGR2B | Fc fragment of IgG, low affinity IIb, receptor for (CD32) |
| FEV | FEV protein - (HSRNAFEV) |
| FGFR1 | fibroblast growth factor receptor 1 |
| FGFR1OP | FGFR1 oncogene partner (FOP) |
| FGFR2 | fibroblast growth factor receptor 2 |
| FGFR3 | fibroblast growth factor receptor 3 |
| FH | fumarate hydratase |
| FHIT | fragile histidine triad gene |
| FIP1L1 | FIP1 like 1 (*S. cerevisiae*) |
| FLI1 | Friend leukemia virus integration 1 |
| FLJ27352 | BX648577, FLJ27352 hypothetical LOC145788 |
| FLT3 | fms-related tyrosine kinase 3 |
| FNBP1 | formin binding protein 1 (FBP17) |
| FOXL2 | forkhead box L2 |
| FOXO1A | forkhead box O1A (FKHR) |
| FOXO3A | forkhead box O3A |
| FOXP1 | forkhead box P1 |
| FSTL3 | follistatin-like 3 (secreted glycoprotein) |
| FUS | fusion, derived from t(12;16) malignant liposarcoma |
| FVT1 | follicular lymphoma variant translocation 1 |
| GAS7 | growth arrest-specific 7 |
| GATA1 | GATA binding protein 1 (globin transcription factor 1) |
| GATA2 | GATA binding protein 2 |
| GATA3 | GATA binding protein 3 |
| GMPS | guanine monphosphate synthetase |
| GNA11 | guanine nucleotide binding protein (G protein), alpha 11 (Gq class) |
| GNAQ | guanine nucleotide binding protein (G protein), q polypeptide |
| GNAS | guanine nucleotide binding protein (G protein), alpha stimulating activity polypeptide 1 |
| GOLGA5 | golgi autoantigen, golgin subfamily a, 5 (PTC5) |
| GOPC | golgi associated PDZ and coiled-coil motif containing |
| GPC3 | glypican 3 |
| GPHN | gephyrin (GPH) |
| GRAF | GTPase regulator associated with focal adhesion kinase pp125(FAK) |
| HCMOGT-1 | sperm antigen HCMOGT-1 |
| HEAB | ATP_GTP binding protein |
| HEI10 | enhancer of invasion 10 - fused to HMGA2 |
| HERPUD1 | homocysteine-inducible, endoplasmic reticulum stress-inducible, ubiquitin-like domain member 1 |
| HIP1 | huntingtin interacting protein 1 |
| HISTIH4I | histone I, H4i (H4FM) |
| HLF | hepatic leukemia factor |
| HLXB9 | homeo box HB9 |
| HMGA1 | high mobility group AT-hook 1 |
| HMGA2 | high mobility group AT-hook 2 (HMGIC) |
| HNRNPA2B1 | heterogeneous nuclear ribonucleoprotein A2/B1 |
| HOOK3 | hook homolog 3 |
| HOXA11 | homeo box A11 |
| HOXA13 | homeo box A13 |
| HOXA9 | homeo box A9 |
| HOXC11 | homeo box C11 |
| HOXC13 | homeo box C13 |
| HOXD11 | homeo box D11 |
| HOXD13 | homeo box D13 |
| HRAS | v-Ha-ras Harvey rat sarcoma viral oncogene homolog |
| HRPT2 | hyperparathyroidism 2 |
| HSPCA | heat shock 90 kDa protein 1, alpha |
| HSPCB | heat shock 90 kDa protein 1, beta |
| IDH1 | isocitrate dehydrogenase 1 (NADP+), soluble |
| IDH2 | socitrate dehydrogenase 2 (NADP+), mitochondrial |
| IGH@ | immunoglobulin heavy locus |
| IGK@ | immunoglobulin kappa locus |
| IGL@ | immunoglobulin lambda locus |
| IKZF1 | IKAROS family zinc finger 1 |
| IL2 | interleukin 2 |
| IL21R | interleukin 21 receptor |
| IL6ST | interleukin 6 signal transducer (gp130, oncostatin M receptor) |

TABLE 1-continued

| | |
|---|---|
| IRF4 | interferon regulatory factor 4 |
| IRTA1 | immunoglobulin superfamily receptor translocation associated 1 |
| ITK | IL2-inducible T-cell kinase |
| JAK1 | Janus kinase 1 |
| JAK2 | Janus kinase 2 |
| JAK3 | Janus kinase 3 |
| JAZF1 | juxtaposed with another zinc finger gene 1 |
| JUN | jun oncogene |
| KDM5A | lysine (K)-specific demethylase 5A, JARID1A |
| KDM5C | lysine (K)-specific demethylase 5C (JARID1C) |
| KDM6A | lysine (K)-specific demethylase 6A, UTX |
| KDR | vascular endothelial growth factor receptor 2 |
| KIAA1549 | KIAA1549 |
| KIT | v-kit Hardy-Zuckerman 4 feline sarcoma viral oncogene homolog |
| KLK2 | kallikrein-related peptidase 2 |
| KRAS | v-Ki-ras2 Kirsten rat sarcoma 2 viral oncogene homolog |
| KTN1 | kinectin 1 (kinesin receptor) |
| LAF4 | lymphoid nuclear protein related to AF4 |
| LASP1 | LIM and SH3 protein 1 |
| LCK | lymphocyte-specific protein tyrosine kinase |
| LCP1 | lymphocyte cytosolic protein 1 (L-plastin) |
| LCX | leukemia-associated protein with a CXXC domain |
| LHFP | lipoma HMGIC fusion partner |
| LIFR | leukemia inhibitory factor receptor |
| LMO1 | LIM domain only 1 (rhombotin 1) (RBTN1) |
| LMO2 | LIM domain only 2 (rhombotin-like 1) (RBTN2) |
| LPP | LIM domain containing preferred translocation partner in lipoma |
| LYL1 | lymphoblastic leukemia derived sequence 1 |
| MADH4 | Homolog of *Drosophila* Mothers Against Decapentaplegic 4 gene |
| MAF | v-maf musculoaponeurotic fibrosarcoma oncogene homolog |
| MAFB | v-maf musculoaponeurotic fibrosarcoma oncogene homolog B (avian) |
| MALT1 | mucosa associated lymphoid tissue lymphoma translocation gene 1 |
| MAML2 | mastermind-like 2 (*Drosophila*) |
| MAP2K4 | mitogen-activated protein kinase kinase 4 |
| MDM2 | Mdm2 p53 binding protein homolog |
| MDM4 | Mdm4 p53 binding protein homolog |
| MDR1/Pgp | Multi-drug resistance protein/P-glycoprotein |
| MDS1 | myelodysplasia syndrome 1 |
| MDS2 | myelodysplastic syndrome 2 |
| MECT1 | mucoepidermoid translocated 1 |
| MEN1 | multiple endocrine neoplasia type I gene |
| MET | met proto-oncogene (hepatocyte growth factor receptor) |
| MHC2TA | MHC class II transactivator |
| MITF | microphthalmia-associated transcription factor |
| MKL1 | megakaryoblastic leukemia (translocation) 1 |
| MLF1 | myeloid leukemia factor 1 |
| MLH1 | *E. coli* MutL homolog gene |
| MLL | myeloid/lymphoid or mixed-lineage leukemia (trithorax homolog, *Drosophila*) |
| MLL2 | myeloid/lymphoid or mixed-lineage leukemia 2 |
| MLL3 | myeloid/lymphoid or mixed-lineage leukemia 3 |
| MLLT1 | myeloid/lymphoid or mixed-lineage leukemia (trithorax homolog, *Drosophila*); translocated to, 1 (ENL) |
| MLLT10 | myeloid/lymphoid or mixed-lineage leukemia (trithorax homolog, *Drosophila*); translocated to, 10 (AF10) |
| MLLT2 | myeloid/lymphoid or mixed-lineage leukemia (trithorax homolog, *Drosophila*); translocated to, 2 (AF4) |
| MLLT3 | myeloid/lymphoid or mixed-lineage leukemia (trithorax homolog, *Drosophila*); translocated to, 3 (AF9) |
| MLLT4 | myeloid/lymphoid or mixed-lineage leukemia (trithorax homolog, *Drosophila*); translocated to, 4 (AF6) |
| MLLT6 | myeloid/lymphoid or mixed-lineage leukemia (trithorax homolog, *Drosophila*); translocated to, 6 (AF17) |
| MLLT7 | myeloid/lymphoid or mixed-lineage leukemia (trithorax homolog, *Drosophila*); translocated to, 7 (AFX1) |
| MN1 | meningioma (disrupted in balanced translocation) 1 |
| MPL | myeloproliferative leukemia virus oncogene, thrombopoietin receptor |
| MRP1 | multiple drug resistance protein 1 |
| MSF | MLL septin-like fusion |
| MSH2 | mutS homolog 2 (*E. coli*) |
| MSH6 | mutS homolog 6 (*E. coli*) |
| MSI2 | musashi homolog 2 (*Drosophila*) |
| MSN | moesin |
| MTCP1 | mature T-cell proliferation 1 |
| MUC1 | mucin 1, transmembrane |
| MUTYH | mutY homolog (*E. coli*) |
| MYB | v-myb myeloblastosis viral oncogene homolog |
| MYC | v-myc myelocytomatosis viral oncogene homolog (avian) |
| MYCL1 | v-myc myelocytomatosis viral oncogene homolog 1, lung carcinoma derived (avian) |
| MYCN | v-myc myelocytomatosis viral related oncogene, neuroblastoma derived (avian) |
| MYD88 | myeloid differentiation primary response gene (88) |
| MYH11 | myosin, heavy polypeptide 11, smooth muscle |
| MYH9 | myosin, heavy polypeptide 9, non-muscle |
| MYST4 | MYST histone acetyltransferase (monocytic leukemia) 4 (MORF) |
| NACA | nascent-polypeptide-associated complex alpha polypeptide |
| NBS1 | Nijmegen breakage syndrome 1 (nibrin) |
| NCOA1 | nuclear receptor coactivator 1 |
| NCOA2 | nuclear receptor coactivator 2 (TIF2) |
| NCOA4 | nuclear receptor coactivator 4 - PTC3 (ELE1) |
| NF1 | neurofibromatosis type 1 gene |
| NF2 | neurofibromatosis type 2 gene |
| NFE2L2 | nuclear factor (erythroid-derived 2)-like 2 (NRF2) |
| NFIB | nuclear factor I/B |
| NFKB2 | nuclear factor of kappa light polypeptide gene enhancer in B-cells 2 (p49/p100) |
| NIN | ninein (GSK3B interacting protein) |
| NKX2-1 | NK2 homeobox 1 |
| NONO | non-POU domain containing, octamer-binding |
| NOTCH1 | Notch homolog 1, translocation-associated (*Drosophila*) (TAN1) |
| NOTCH2 | Notch homolog 2 |
| NPM1 | nucleophosmin (nucleolar phosphoprotein B23, numatrin) |
| NR4A3 | nuclear receptor subfamily 4, group A, member 3 (NOR1) |
| NRAS | neuroblastoma RAS viral (v-ras) oncogene homolog |
| NSD1 | nuclear receptor binding SET domain protein 1 |
| NTRK1 | neurotrophic tyrosine kinase, receptor, type 1 |
| NTRK3 | neurotrophic tyrosine kinase, receptor, type 3 |
| NUMA1 | nuclear mitotic apparatus protein 1 |
| NUP214 | nucleoporin 214 kDa (CAN) |
| NUP98 | nucleoporin 98 kDa |
| NUT | nuclear protien in testis |
| OLIG2 | oligodendrocyte lineage transcription factor 2 (BHLHB1) |
| OMD | osteomodulin |
| P2RY8 | purinergic receptor P2Y, G-protein coupled, 8 |
| PAFAH1B2 | platelet-activating factor acetylhydrolase, isoform Ib, beta subunit 30 kDa |
| PALB2 | partner and localizer of BRCA2 |
| PARP-1 | poly [ADP-ribose] polymerase 1 |
| PAX3 | paired box gene 3 |
| PAX5 | paired box gene 5 (B-cell lineage specific activator protein) |
| PAX7 | paired box gene 7 |
| PAX8 | paired box gene 8 |
| PBRM1 | polybromo 1 |
| PBX1 | pre-B-cell leukemia transcription factor 1 |
| PCM1 | pericentriolar material 1 (PTC4) |
| PCSK7 | proprotein convertase subtilisin/kexin type 7 |
| PDE4DIP | phosphodiesterase 4D interacting protein (myomegalin) |
| PDGFB | platelet-derived growth factor beta polypeptide (simian sarcoma viral (v-sis) oncogene homolog) |
| PDGFRA | platelet-derived growth factor, alpha-receptor |
| PDGFRB | platelet-derived growth factor receptor, beta polypeptide |
| PER1 | period homolog 1 (*Drosophila*) |
| PHOX2B | paired-like homeobox 2b |
| PICALM | phosphatidylinositol binding clathrin assembly protein (CALM) |
| PIK3CA | phosphoinositide-3-kinase, catalytic, alpha polypeptide |
| PIK3R1 | phosphoinositide-3-kinase, regulatory subunit 1 (alpha) |
| PIM1 | pim-1 oncogene |
| PLAG1 | pleiomorphic adenoma gene 1 |
| PML | promyelocytic leukemia |
| PMS1 | PMS1 postmeiotic segregation increased 1 (*S. cerevisiae*) |
| PMS2 | PMS2 postmeiotic segregation increased 2 (*S. cerevisiae*) |
| PMX1 | paired mesoderm homeo box 1 |
| PNUTL1 | peanut-like 1 (*Drosophila*) |
| POU2AF1 | POU domain, class 2, associating factor 1 (OBF1) |
| POU5F1 | POU domain, class 5, transcription factor 1 |
| PPARG | peroxisome proliferative activated receptor, gamma |

TABLE 1-continued

| | |
|---|---|
| PPP2R1A | protein phosphatase 2, regulatory subunit A, alpha |
| PRCC | papillary renal cell carcinoma (translocation-associated) |
| PRDM1 | PR domain containing 1, with ZNF domain |
| PRDM16 | PR domain containing 16 |
| PRF1 | perforin 1 (pore forming protein) |
| PRKAR1A | protein kinase, cAMP-dependent, regulatory, type I, alpha (tissue specific extinguisher 1) |
| PRO1073 | PRO1073 protein (ALPHA) |
| PSIP2 | PC4 and SFRS1 interacting protein 2 (LEDGF) |
| PTCH | Homolog of Drosophila Patched gene |
| PTEN | phosphatase and tensin homolog gene |
| PTPN11 | protein tyrosine phosphatase, non-receptor type 11 |
| RAB5EP | rabaptin, RAB GTPase binding effector protein 1 (RABPT5) |
| RAD51L1 | RAD51-like 1 (S. cerevisiae) (RAD51B) |
| RAF1 | v-raf-1 murine leukemia viral oncogene homolog 1 |
| RALGDS | ral guanine nucleotide dissociation stimulator |
| RANBP17 | RAN binding protein 17 |
| RAP1GDS1 | RAP1, GTP-GDP dissociation stimulator 1 |
| RARA | retinoic acid receptor, alpha |
| RB1 | retinoblastoma gene |
| RBM15 | RNA binding motif protein 15 |
| RECQL4 | RecQ protein-like 4 |
| REL | v-rel reticuloendotheliosis viral oncogene homolog (avian) |
| RET | ret proto-oncogene |
| ROS1 | v-ros UR2 sarcoma virus oncogene homolog 1 (avian) |
| RPL22 | ribosomal protein L22 (EAP) |
| RPN1 | ribophorin I |
| RUNDC2A | RUN domain containing 2A |
| RUNX1 | runt-related transcription factor 1 (AML1) |
| RUNXBP2 | runt-related transcription factor binding protein 2 (MOZ/ZNF220) |
| SBDS | Shwachman-Bodian-Diamond syndrome protein |
| SDH5 | chromosome 11 open reading frame 79 |
| SDHB | succinate dehydrogenase complex, subunit B, iron sulfur (Ip) |
| SDHC | succinate dehydrogenase complex, subunit C, integral membrane protein, 15 kDa |
| SDHD | succinate dehydrogenase complex, subunit D, integral membrane protein |
| SEPT6 | septin 6 |
| SET | SET translocation |
| SETD2 | SET domain containing 2 |
| SFPQ | splicing factor proline/glutamine rich(polypyrimidine tract binding protein associated) |
| SFRS3 | splicing factor, arginine/serine-rich 3 |
| SH3GL1 | SH3-domain GRB2-like 1 (EEN) |
| SIL | TAL1 (SCL) interrupting locus |
| SLC45A3 | solute carrier family 45, member 3 |
| SMARCA4 | SWI/SNF related, matrix associated, actin dependent regulator of chromatin, subfamily a, member 4 |
| SMARCB1 | SWI/SNF related, matrix associated, actin dependent regulator of chromatin, subfamily b, member 1 |
| SMO | smoothened homolog (Drosophila) |
| SOCS1 | suppressor of cytokine signaling 1 |
| SOX2 | SRY (sex determining region Y)-box 2 |
| SRGAP3 | SLIT-ROBO Rho GTPase activating protein 3 |
| SS18 | synovial sarcoma translocation, chromosome 18 |
| SS18L1 | synovial sarcoma translocation gene on chromosome 18-like 1 |
| SSH3BP1 | spectrin SH3 domain binding protein 1 |
| SSX1 | synovial sarcoma, X breakpoint 1 |
| SSX2 | synovial sarcoma, X breakpoint 2 |
| SSX4 | synovial sarcoma, X breakpoint 4 |
| STK11 | serine/threonine kinase 11 gene (LKB1) |
| STL | Six-twelve leukemia gene |
| SUFU | suppressor of fused homolog (Drosophila) |

TABLE 1-continued

| | |
|---|---|
| SUZ12 | suppressor of zeste 12 homolog (Drosophila) |
| SYK | spleen tyrosine kinase |
| TAF15 | TAF15 RNA polymerase II, TATA box binding protein (TBP)-associated factor, 68 kDa |
| TAL1 | T-cell acute lymphocytic leukemia 1 (SCL) |
| TAL2 | T-cell acute lymphocytic leukemia 2 |
| TCEA1 | transcription elongation factor A (SII), 1 |
| TCF1 | transcription factor 1, hepatic (HNF1) |
| TCF12 | transcription factor 12 (HTF4, helix-loop-helix transcription factors 4) |
| TCF3 | transcription factor 3 (E2A immunoglobulin enhancer binding factors E12/E47) |
| TCL1A | T-cell leukemia/lymphoma 1A |
| TCL6 | T-cell leukemia/lymphoma 6 |
| TET2 | tet oncogene family member 2 |
| TFE3 | transcription factor binding to IGHM enhancer 3 |
| TFEB | transcription factor EB |
| TFG | TRK-fused gene |
| TFPT | TCF3 (E2A) fusion partner (in childhood Leukemia) |
| TFRC | transferrin receptor (p90, CD71) |
| THRAP3 | thyroid hormone receptor associated protein 3 (TRAP150) |
| TIF1 | transcriptional intermediary factor 1 (PTC6, TIF1A) |
| TLX1 | T-cell leukemia, homeobox 1 (HOX11) |
| TLX3 | T-cell leukemia, homeobox 3 (HOX11L2) |
| TMPRSS2 | transmembrane protease, serine 2 |
| TNFAIP3 | tumor necrosis factor, alpha-induced protein 3 |
| TNFRSF14 | tumor necrosis factor receptor superfamily, member 14 (herpesvirus entry mediator) |
| TNFRSF17 | tumor necrosis factor receptor superfamily, member 17 |
| TNFRSF6 | tumor necrosis factor receptor superfamily, member 6 (FAS) |
| TOP1 | topoisomerase (DNA) I |
| TP53 | tumor protein p53 |
| TPM3 | tropomyosin 3 |
| TPM4 | tropomyosin 4 |
| TPR | translocated promoter region |
| TRA@ | T cell receptor alpha locus |
| TRB@ | T cell receptor beta locus |
| TRD@ | T cell receptor delta locus |
| TRIM27 | tripartite motif-containing 27 |
| TRIM33 | tripartite motif-containing 33 (PTC7, TIF1G) |
| TRIP11 | thyroid hormone receptor interactor 11 |
| TSC1 | tuberous sclerosis 1 gene |
| TSC2 | tuberous sclerosis 2 gene |
| TSHR | thyroid stimulating hormone receptor |
| TTL | tubulin tyrosine ligase |
| USP6 | ubiquitin specific peptidase 6 (Tre-2 oncogene) |
| VHL | von Hippel-Lindau syndrome gene |
| WAS | Wiskott-Aldrich syndrome |
| WHSC1 | Wolf-Hirschhorn syndrome candidate 1(MMSET) |
| WHSC1L1 | Wolf-Hirschhorn syndrome candidate 1-like 1 (NSD3) |
| WIF1 | WNT inhibitory factor 1 |
| WRN | Werner syndrome (RECQL2) |
| WT1 | Wilms tumour 1 gene |
| WTX | family with sequence similarity 123B (FAM123B) |
| XPA | xeroderma pigmentosum, complementation group A |
| XPC | xeroderma pigmentosum, complementation group C |
| ZNF145 | zinc finger protein 145 (PLZF) |
| ZNF198 | zinc finger protein 198 |
| ZNF278 | zinc finger protein 278 (ZSG) |
| ZNF331 | zinc finger protein 331 |
| ZNF384 | zinc finger protein 384 (CIZ/NMP4) |
| ZNF521 | zinc finger protein 521 |
| ZNF9 | zinc finger protein 9 (a cellular retroviral nucleic acid binding protein) |
| ZNFN1A1 | zinc finger protein, subfamily 1A, 1 (Ikaros) |

We claim:

1. A targeted particle comprising:
    (a) a plurality of landscape phage fusion proteins comprising a filamentous phage pVIII major coat protein displaying a heterologous peptide, the heterologous peptide capable of directing binding of the targeted particle to a specific target site,
    (b) a heterologous nucleic acid that is 10-50 nucleotides in length, and
    (c) no more than 5% (w/w) phospholipids, wherein the targeted particle comprises a molar excess of the landscape fusion proteins relative to the heterologous nucleic acid within a range of 60-fold to 100-fold, and wherein the targeted particle is formed by self-assembly in vitro of complexes formed between the plurality of landscape phage fusion proteins and the heterologous nucleic acid, such that the landscape phage fusion proteins encapsulate the nucleic acid in the particle so as to protect the nucleic acid from degradation and allow delivery of the heterologous nucleic acid to the target site.

2. The targeted particle of claim 1, wherein the heterologous nucleic acid is siRNA.

3. The targeted particle of claim 1, wherein the heterologous peptide comprises no more than 9 amino acids.

4. The targeted particle of claim 1, wherein the targeted particle binds specifically to cancer cells.

5. The targeted particle of claim 4, wherein the cancer cells are breast cancer cells.

6. The targeted particle of claim 1, wherein the heterologous nucleic acid is siRNA that inhibits expression of a gene selected from a group consisting of ABI1, ABL2, ACSL6, AF1Q, AF5Q31, AKT1, AKT2, ARNT, ASPSCR1, ATF1, ATIC, BCL10, BCRP, BFHD, BIRC3, BMPR1A, BTG1, CBFA2T1, CBFA2T3, CBFB, CCND1, CDC2, CDK4, CHIC2, CHN1, COPEB, COX6C, CTNNB1, CYLD, DDB2, DDIT3, DEK, Eif4a, EIF4A2, EPS15, ERBB2, ERCC2, ERCC3, ERCC5, ERG, ETV4, ETV6, EWSR1, EXT1, EXT2, FANCC, FANCG, EGER1OP, FGFR3, FH, FIP1L1, FUS, GAS7, GATA1, GMPS, GOLGA5, GPC (gene), GPHN, HIST1H4I, HRAS, HSPCA, IL21R, IIRF4, KRAS2, LASP1, LCP1, LHFP, LMO2, LYL1, MADH4, MDR1/Pgp, MEIS1, MLF1, MLH1, MLLT3, MLLT6, MNAT1, MRP1, MSF, MSH2, MSN, MUTYH, MYC, MYCL1, MYCN, NCOA4, NF2, NPM1, NRAS, PARP1, PAX8, PCBD, PDGFB, PHOX2B, PIM1, PLK2, PNUTL1, POU2F1, PPARG, PRCC, PRKACB, PRKAR1A, PTEN, PTPN11, RABEP1, RAD51L1, RAP1GDS1, RARA, RBI, REL, RET, RHOH, RPL22, SBDS, SDHB, SEPTIN6, SET, SH3GL1, SS18L1, SSX1, SSX2, SSX4, STAT3, TAF15, TCF12, TCL1A, TFE3, TFEB, TFG, TFPT, TFRC, TNFRSF6, TP53, TPM3, TPM4, TRIP11, VHL, WAS, WT1, ZNF198, ZNF278, ZNF384, and ZNFN1A.

7. The targeted particle of claim 1, wherein the heterologous nucleic acid is siRNA that inhibits gene expression of a gene selected from PARP1, MDR1/Pgp, MRP1, and BCRP.

8. A pharmaceutical composition comprising:
(a) the targeted particle of claim 1; and
(b) a pharmaceutical carrier, excipient, or diluent.

9. A method for inhibiting expression of a gene in a cell comprising contacting the cell with the targeted particle of claim 1, the targeted particle binding specifically to the cell and comprising a siRNA that inhibits expression of the gene.

10. A method for forming the targeted particle of claim 1, the method comprising:
(a) obtaining bacteriophage comprising a plurality of fusion proteins displaying a binding peptide for a desired target site;
(b) treating the bacteriophage with a denaturing agent and isolating or purifying the fusion proteins from the treated bacteriophage;
(c) preparing a mixture of the isolated or purified fusion proteins and a heterologous nucleic acid that is 10-50 nucleotides in length to form the targeted particle; and
(d) purifying the targeted particle from the mixture.

11. A method for forming the targeted particle of claim 1, the method comprising:
(a) preparing a mixture of
(i) a solution of isolated or purified landscape phage fusion proteins displaying a binding peptide for a desired target site, wherein the fusion proteins are in non-assembled form and
(ii) a solution of isolated or purified heterologous nucleic acid that is 10-50 nucleotides in length, wherein the targeted particle forms in the mixture; and
(b) isolating or purifying the targeted particle from the mixture.

12. The method of claim 10, wherein the heterologous nucleic acid is siRNA.

13. The method of claim 12, wherein the mixture comprises at east a 10-fold molar excess of the fusion proteins relative to the siRNA.

14. A targeted particle consisting of:
(a) a plurality of landscape phage fusion proteins consisting of a filamentous phage pVIII major coat protein displaying a heterologous peptide, the heterologous peptide capable of directing binding of the particle to a specific target site, and
(b) a heterologous nucleic acid that is 10-50 nucleotides in length,
wherein the targeted particle comprises a molar excess of the landscape fusion protein relative to the heterologous nucleic acid within a range of 60-fold to 100-fold, and
wherein the targeted particle is formed by self-assembly in vitro of complexes formed between the plurality of landscape phage fusion proteins and the heterologous nucleic acid, such that the landscape phage fusion proteins encapsulate the nucleic acid in the particle so as to protect the nucleic acid from degradation and allow delivery of the heterologous nucleic acid to the target site.

15. A targeted particle consisting of:
(a) a plurality of landscape phage fusion proteins consisting of a filamentous phage pVIII major coat protein displaying a heterologous peptide, the heterologous peptide capable of directing binding of the particle to a specific target site, and
(b) siRNA that is 15-50 nucleotides in length,
wherein the targeted particle the targeted particle comprises a molar excess of the landscape fusion protein relative to the siRNA within a range of 60-fold to 100-fold, and
wherein the targeted particle is formed by self-assembly in vitro of complexes formed between the plurality of landscape phage fusion proteins and the siRNA, such that the landscape phage fusion proteins encapsulate the siRNA in the particle so as to protect the siRNA from degradation and allow delivery of the siRNA to the target site.

* * * * *

SEQUENCE LISTING

<160> NUMBER OF SEQ ID NOS: 8

<210> SEQ ID NO 1
<211> LENGTH: 73
<212> TYPE: PRT

<213> ORGANISM: Bacteriophage f1

<400> SEQUENCE: 1

Met Lys Lys Ser Leu Val Leu Lys Ala Ser Val Ala Val Ala Thr Leu
1               5                   10                  15

Val Pro Met Leu Ser Phe Ala Ala Glu Gly Glu Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
50                  55                  60

Phe Lys Lys Phe Thr Ser Lys Ala Ser
65                  70

<210> SEQ ID NO 2
<211> LENGTH: 50
<212> TYPE: PRT
<213> ORGANISM: Bacteriophage f1

<400> SEQUENCE: 2

Ala Glu Gly Glu Asp Pro Ala Lys Ala Ala Phe Asp Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50

<210> SEQ ID NO 3
<211> LENGTH: 55
<212> TYPE: PRT
<213> ORGANISM: Artificial
<220> FEATURE:
<223> OTHER INFORMATION: Bacteriophage f1 library having random 8-mer
      insert in pVIII major coat protein
<220> FEATURE:
<221> NAME/KEY: misc_feature
<222> LOCATION: (2)..(9)
<223> OTHER INFORMATION: Xaa can be any naturally occurring amino acid

<400> SEQUENCE: 3

Ala Xaa Xaa Xaa Xaa Xaa Xaa Xaa Asp Pro Ala Lys Ala Ala Phe
1               5                   10                  15

Asp Ser Leu Gln Ala Ser Ala Thr Glu Tyr Ile Gly Tyr Ala Trp Ala
            20                  25                  30

Met Val Val Val Ile Val Gly Ala Thr Ile Gly Ile Lys Leu Phe Lys
        35                  40                  45

Lys Phe Thr Ser Lys Ala Ser
    50                  55

<210> SEQ ID NO 4
<211> LENGTH: 55
<212> TYPE: PRT
<213> ORGANISM: Artificial
<220> FEATURE:
<223> OTHER INFORMATION: Bacteriophage f1 library having random 9-mer
      insert in pVIII major coat protein
<220> FEATURE:
<221> NAME/KEY: misc_feature
<222> LOCATION: (2)..(10)
<223> OTHER INFORMATION: Xaa can be any naturally occurring amino acid

```
<400> SEQUENCE: 4

Ala Xaa Xaa Xaa Xaa Xaa Xaa Xaa Xaa Pro Ala Lys Ala Ala Phe
1               5                   10                  15

Asp Ser Leu Gln Ala Ser Ala Thr Glu Tyr Ile Gly Tyr Ala Trp Ala
            20                  25                  30

Met Val Val Ile Val Gly Ala Thr Ile Gly Ile Lys Leu Phe Lys
        35                  40                  45

Lys Phe Thr Ser Lys Ala Ser
    50                  55

<210> SEQ ID NO 5
<211> LENGTH: 19
<212> TYPE: RNA
<213> ORGANISM: Artificial
<220> FEATURE:
<223> OTHER INFORMATION: Sense siRNA targeted to human PARP-1 mRNA

<400> SEQUENCE: 5
ggaugaucuu cgacgugga                                                    19

<210> SEQ ID NO 6
<211> LENGTH: 19
<212> TYPE: RNA
<213> ORGANISM: Artificial
<220> FEATURE:
<223> OTHER INFORMATION: Antisense siRNA targeted to human PARP-1 mRNA

<400> SEQUENCE: 6
uccacgucga agaucaucc                                                    19

<210> SEQ ID NO 7
<211> LENGTH: 9
<212> TYPE: PRT
<213> ORGANISM: Artificial
<220> FEATURE:
<223> OTHER INFORMATION: Peptide insert in bacteriophage f1 library of
      SEQ ID NO:4 selected for specific binding to MCF-7 breast cancer
      cells

<400> SEQUENCE: 7

Val Glu Glu Gly Gly Tyr Ile Ala Ala
1               5

<210> SEQ ID NO 8
<211> LENGTH: 8
<212> TYPE: PRT
<213> ORGANISM: Artificial
<220> FEATURE:
<223> OTHER INFORMATION: Peptide insert in bacteriophage f1 library of
      SEQ ID NO:3

<400> SEQUENCE: 8

Val Pro Glu Gly Ala Phe Ser Ser
1               5
```